(12) United States Patent
Rawlins et al.

(10) Patent No.: US 6,720,347 B2
(45) Date of Patent: Apr. 13, 2004

(54) CARBON SUBSTITUTED AMINOTHIAZOLE INHIBITORS OF CYCLIN DEPENDENT KINASES

(75) Inventors: David B. Rawlins, Morrisville, PA (US); S. David Kimball, E. Windsor, NJ (US); Kyoung S. Kim, North Brunswick, NJ (US); Raj N. Misra, Hopewell, NJ (US); Kevin R. Webster, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/112,133

(22) Filed: Mar. 29, 2002

(65) Prior Publication Data

US 2002/0165259 A1 Nov. 7, 2002

Related U.S. Application Data

(62) Division of application No. 09/329,616, filed on Jun. 10, 1999, now Pat. No. 6,407,124.
(60) Provisional application No. 60/089,747, filed on Jun. 18, 1998.

(51) Int. Cl.[7] .................... A61K 31/426; C07D 417/06
(52) U.S. Cl. .................... 514/371; 546/270.7; 548/195; 514/342
(58) Field of Search ...................... 548/195; 546/270.7; 514/342, 371

(56) References Cited

U.S. PATENT DOCUMENTS

| | | | | |
|---|---|---|---|---|
| 3,169,954 A | 2/1965 | Straley et al. | ............... | 260/158 |
| 4,321,372 A | 3/1982 | Kadin | | |
| 5,036,053 A | 7/1991 | Himmelsbach et al. | | |
| 5,254,679 A | * 10/1993 | Bradbury et al. | ........... | 540/221 |
| 5,593,985 A | 1/1997 | Kim et al. | | |

FOREIGN PATENT DOCUMENTS

| | | |
|---|---|---|
| BE | 835.392 | 5/1976 |
| BE | 863.588 | 8/1978 |
| DE | 2756113 A1 | 6/1979 |
| DE | 19506652 A1 | 8/1996 |
| EP | 0030630 | 6/1981 |
| EP | 0337263 A2 | 10/1989 |
| EP | 0516069 A1 | 12/1992 |
| EP | 0716087 A1 | 6/1996 |
| JP | 46018564 B4 * | 5/1971 |
| JP | 07149745 A | 6/1995 |
| JP | 07149746 A | 6/1995 |
| JP | 08048628 | 2/1996 |
| JP | 09160176 A | 6/1997 |
| JP | 09235278 A | 9/1997 |
| WO | WO93/06127 | 4/1993 |
| WO | WO95/32210 | 11/1995 |
| WO | WO98/04536 | 5/1998 |
| WO | WO00/26202 | 11/2000 |
| WO | WO00/26203 | 11/2000 |

OTHER PUBLICATIONS

Saldabols et al., CA 72:21633, 1970.*
Hasekawa et al., CA 77:87100, 1972.*
Goro, A. et al, "Nitroheterocyclic Antimicrobial Agents. 1. Nitrothiazolecarboxaldehyde Derivatives", J. Med. Chem., 1969, 12, 374–379.
Pazzi, P.V. et al, "$H_2$–Antagonists: Synthesis and Activity of 2–Amino–5–Thiazolyl Derivatives",Il Farmaco, 44(11), 1011–1030, 1989.
Erlenmeyer et al., Helvetica Chimica Acta, 1995, vol. 38, No. 5, 1291–1294.
Erlenmeyer et al., Helvetica Chimica Acta, 1949, vol. 32, No. 1, 35–38.
Ferrand et al., European Journal of Medicinal Chemistry—Chimica Therapeutica, 1975, vol. 10, No. 6, 549–556.
Chemical Abstracts, 1973, vol. 78, No. 9, p. 517, 58365z.
Birkinshaw et al., Journal of the Chemical Society, Perkin Transactions 1, 1982, 939–943.
Database Crossfire Beilstein, Beilstein Registry No. 8007698, 1999.

* cited by examiner

*Primary Examiner*—Laura L. Stockton
(74) *Attorney, Agent, or Firm*—Elliott Korsen

(57) ABSTRACT

Compounds of the formula

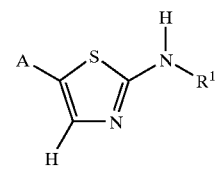

and pharmaceutically acceptable salts thereof, wherein $R^1$ and A are defined herein, are protein kinase inhibitors and are useful in the treatment of proliferative diseases, for example, cancer, inflammation and arthritis. They may also be useful in the treatment of Alzheimer's disease and cardiovascular disease.

2 Claims, 20 Drawing Sheets

Figure 1

| Example | Structure | Molecular Formula | MS (M+H)+ | Procedure of Example |
|---|---|---|---|---|
| 7 | 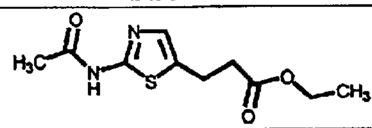 | $C_{10}H_{14}N_2O_3S$ | 243 | 3 |
| 8 | 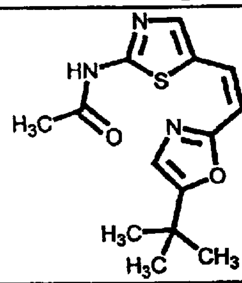 | $C_{14}H_{17}N_3O_2S$ | 292 | 2 |
| 9 | 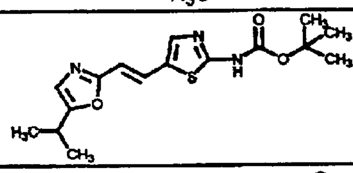 | $C_{16}H_{21}N_3O_3S$ | 336 | 2 |
| 10 | 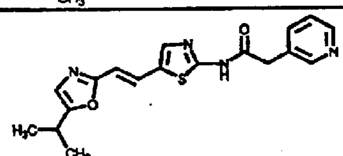 | $C_{18}H_{18}N_4O_2S$ | 355 | 4 |
| 11 | 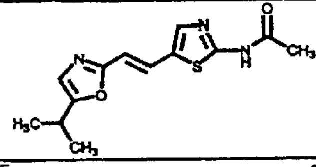 | $C_{13}H_{15}N_3O_2S$ | 278 | 4 |
| 12 | 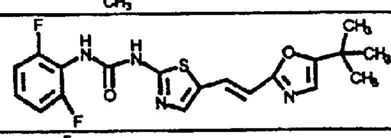 | $C_{19}H_{18}F_2N_4O_2S$ | 405 | 4 |
| 13 | 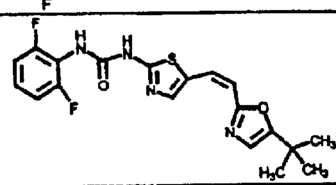 | $C_{19}H_{18}F_2N_4O_2S$ | 405 | 4 |
| 14 | 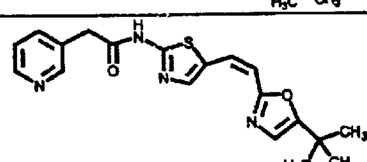 | $C_{19}H_{20}N_4O_2S$ | 369 | 4 |

| Example | Structure | Molecular Formula | MS (M+H)+ | Procedure of Example |
|---|---|---|---|---|
| 15 | 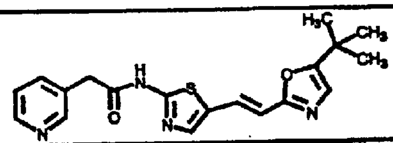 | $C_{19}H_{20}N_4O_2S$ | 369 | 4 |
| 16 | 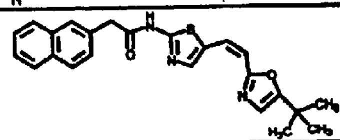 | $C_{24}H_{23}N_3O_2S$ | 419 | 4 |
| 17 | 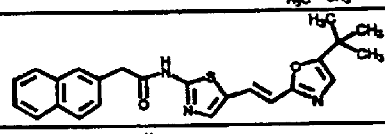 | $C_{24}H_{23}N_3O_2S$ | 419 | 4 |
| 18 | 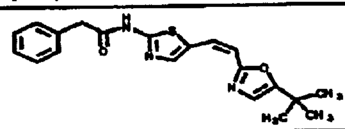 | $C_{20}H_{21}N_3O_2S$ | 368 | 4 |
| 19 | 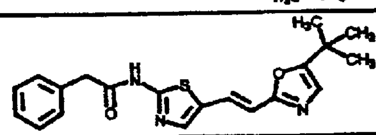 | $C_{20}H_{21}N_3O_2S$ | 368 | 4 |
| 20 | 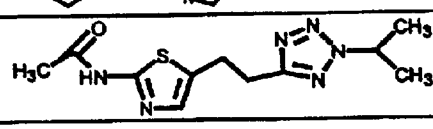 | $C_{11}H_{16}N_6OS$ | 281 | 3 |
| 21 | 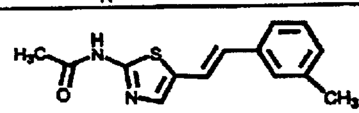 | $C_{14}H_{14}N_2OS$ | 259 | 2 |
| 22 | 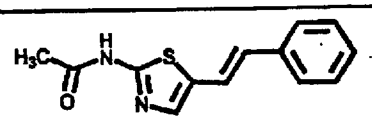 | $C_{13}H_{12}N_2OS$ | 245 | 2 |
| 23 | 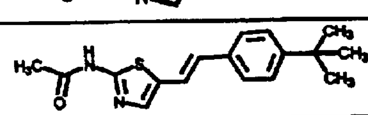 | $C_{17}H_{20}N_2OS$ | 301 | 2 |
| 24 | 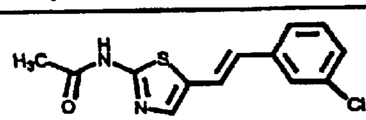 | $C_{13}H_{11}ClN_2OS$ | 280 | 2 |
| 25 | 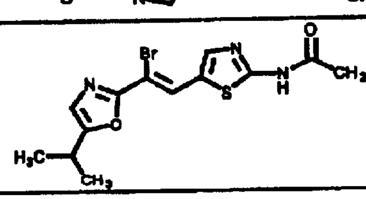 | $C_{13}H_{14}BrN_3O_2S$ | 357 | 2 |

Figure 3

| Example | Structure | Molecular Formula | MS (M+H)+ | Procedure of Example |
|---|---|---|---|---|
| 26 | 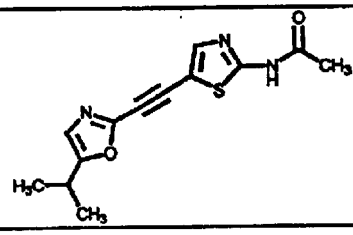 | $C_{13}H_{13}N_3O_2S$ | 276 | 5 |
| 27 | 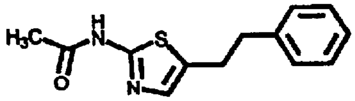 | $C_{13}H_{14}N_2OS$ | 247 | 3 |
| 28 | 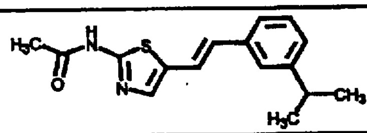 | $C_{16}H_{18}N_2OS$ | 287 | 2 |
| 29 | 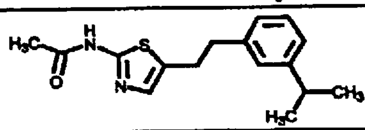 | $C_{16}H_{20}N_2OS$ | 289 | 3 |
| 30 | 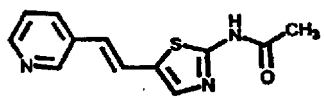 | $C_{12}H_{11}N_3OS$ | 246 | 2 |
| 31 | 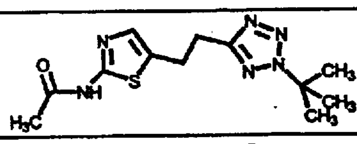 | $C_{12}H_{18}N_6OS$ | 295 | 3 |
| 32 | 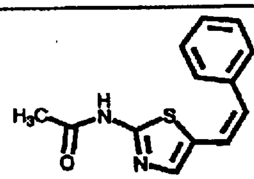 | $C_{13}H_{12}N_2OS$ | 245 | 4 |
| 33 | 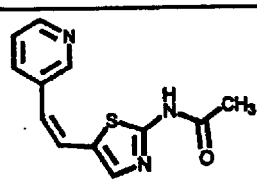 | $C_{12}H_{11}N_3OS$ | 246 | 4 |
| 34 | 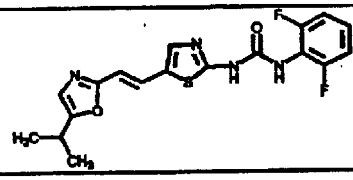 | $C_{18}H_{16}F_2N_4O_2S$ | 391 | 4 |

Figure 4

| Example | Structure | Molecular Formula | MS (M+H)$^+$ | Procedure of Example |
|---|---|---|---|---|
| 35 | 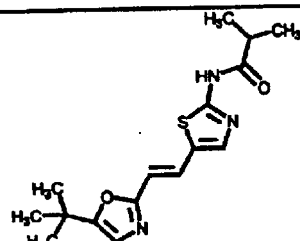 | $C_{16}H_{21}N_3O_2S$ | 320 | 4 |
| 36 | 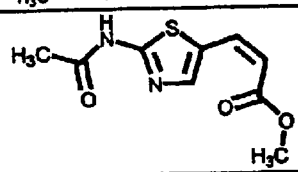 | $C_9H_{10}N_2O_3S$ | 227 | 2 |
| 37 | 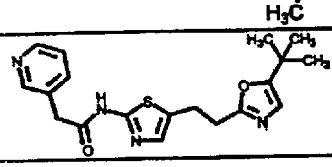 | $C_{19}H_{22}N_4O_2S$ | 371 | 3 |
| 38 | 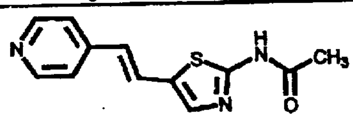 | $C_{12}H_{11}N_3OS$ | 246 | 2 |
| 39 | 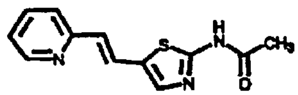 | $C_{12}H_{11}N_3OS$ | 246 | 2 |
| 40 | 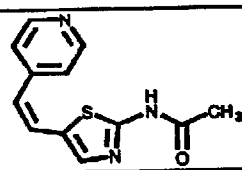 | $C_{12}H_{11}N_3OS$ | 246 | 2 |
| 41 | 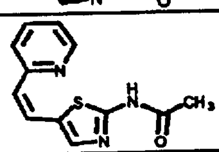 | $C_{12}H_{11}N_3OS$ | 246 | 2 |
| 42 | 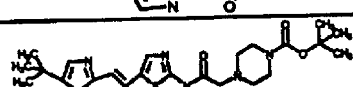 | $C_{23}H_{33}N_5O_4S$ | 477 | 4 |
| 43 | 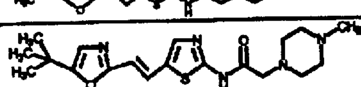 | $C_{19}H_{27}N_5O_2S$ | 391 | 4 |
| 44 | 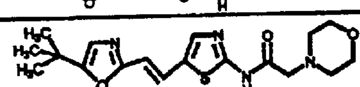 | $C_{18}H_{24}N_4O_3S$ | 377 | 4 |

Figure 5

| Example | Structure | Molecular Formula | MS (M+H)⁺ | Procedure of Example |
|---|---|---|---|---|
| 45 | 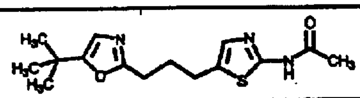 | $C_{15}H_{21}N_3O_2S$ | 308 | 3 |
| 46 | 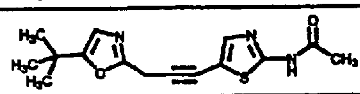 | $C_{15}H_{17}N_3O_2S$ | 304 | 5 |
| 47 | 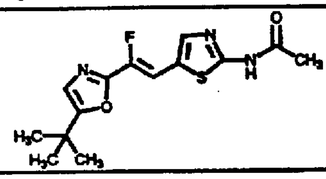 | $C_{14}H_{16}FN_3O_2S$ | 310 | 2 |
| 48 | 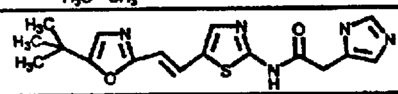 | $C_{17}H_{19}N_5O_2S$ | 358 | 4 |
| 49 | 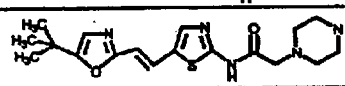 | $C_{18}H_{25}N_5O_2S$ | 377 | 4 |
| 50 | 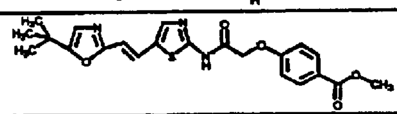 | $C_{22}H_{23}N_3O_5S$ | 443 | 4 |
| 51 | 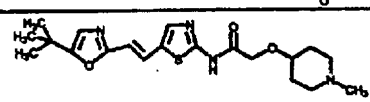 | $C_{20}H_{28}N_4O_3S$ | 406 | 4 |
| 52 | 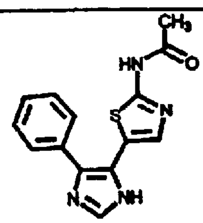 | $C_{14}H_{12}N_4OS$ | 285 | |
| 53 | 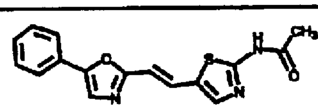 | $C_{16}H_{13}N_3O_2S$ | 312 | 2 |
| 54 | 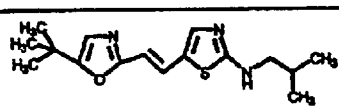 | $C_{16}H_{23}N_3OS$ | 306 | 6 |
| 55 | 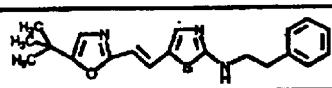 | $C_{20}H_{23}N_3OS$ | 354 | 6 |
| 56 | 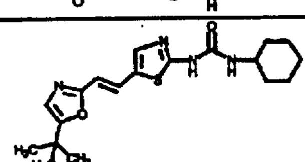 | $C_{19}H_{26}N_4O_2S$ | 376 | 4 |

Figure 6

| Example | Structure | Molecular Formula | MS (M+H)+ | Procedure of Example |
|---|---|---|---|---|
| 57 | 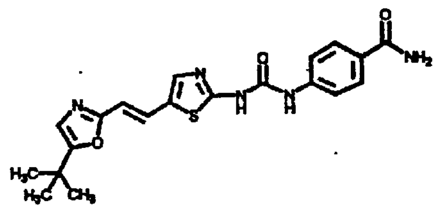 | C20 H21 N5 O3 S | 412 | 4 |
| 58 | 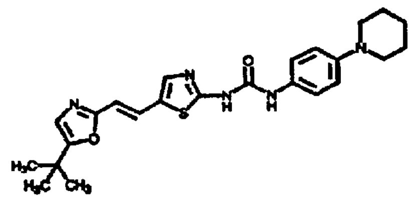 | C24 H29 N5 O2 S | 453 | 4 |
| 59 | 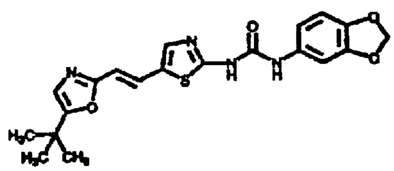 | C20 H20 N4 O4 S | 413 | 4 |
| 60 | 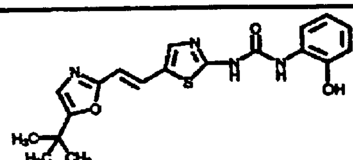 | C19 H20 N4 O3 S | 385 | 4 |
| 61 | 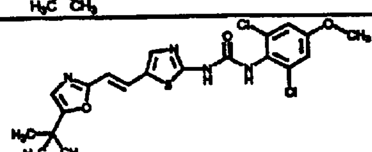 | C20 H20 Cl2 N4 O3 S | 468 | 4 |
| 62 | 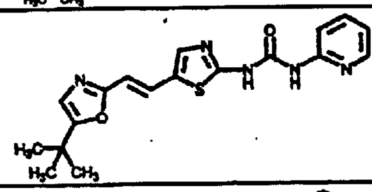 | C18 H19 N5 O2 S | 370 | 4 |
| 63 | 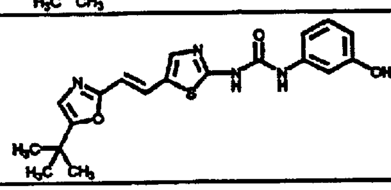 | C19 H20 N4 O3 S | 385 | 4 |

Figure 7

| Example | Structure | Molecular Formula | MS (M+H)+ | Procedure of Example |
|---|---|---|---|---|
| 64 | 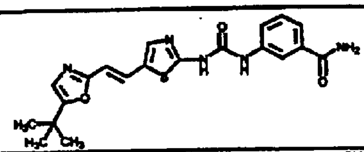 | $C_{20}H_{21}N_5O_3S$ | 412 | 4 |
| 65 | 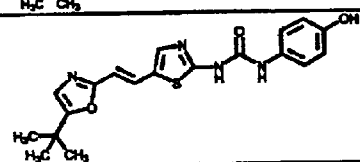 | $C_{19}H_{20}N_4O_3S$ | 385 | 4 |
| 66 | 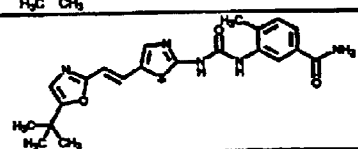 | $C_{21}H_{23}N_5O_3S$ | 427 | 4 |
| 67 | 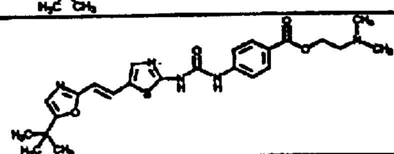 | $C_{24}H_{29}N_5O_4S$ | 485 | 4 |
| 68 | 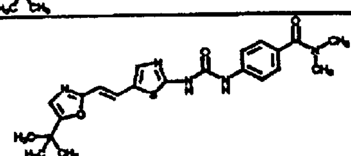 | $C_{22}H_{25}N_5O_3S$ | 441 | 4 |
| 69 | 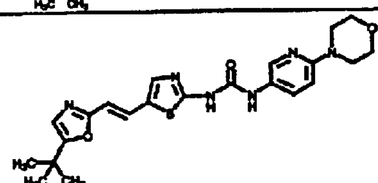 | $C_{22}H_{26}N_6O_3S$ | 456 | 4 |
| 70 | 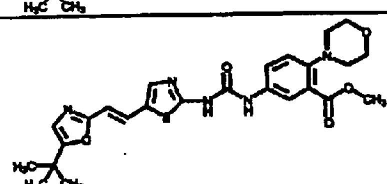 | $C_{25}H_{29}N_5O_5S$ | 513 | 4 |
| 71 | 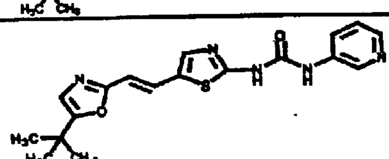 | $C_{18}H_{19}N_5O_2S$ | 370 | 4 |
| 72 | 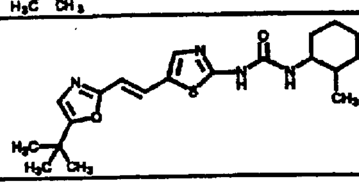 | $C_{20}H_{28}N_4O_2S$ | 390 | 4 |

Figure 8

| Example | Structure | Molecular Formula | MS (M+H)+ | Procedure of Example |
|---|---|---|---|---|
| 73 | 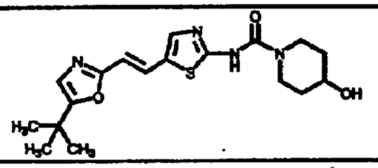 | $C_{18}H_{24}N_4O_3S$ | 377 | 4 |
| 74 | 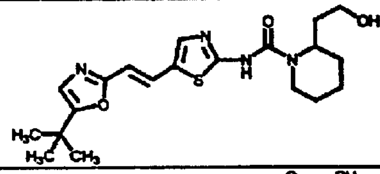 | $C_{20}H_{28}N_4O_3S$ | 406 | 4 |
| 75 | 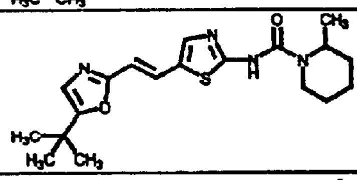 | $C_{19}H_{26}N_4O_2S$ | 376 | 4 |
| 76 | 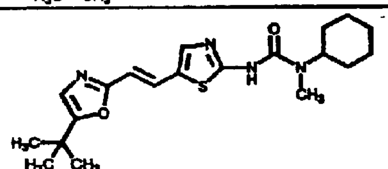 | $C_{20}H_{28}N_4O_2S$ | 390 | 4 |
| 77 | 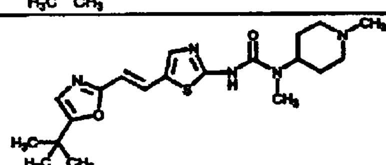 | $C_{20}H_{29}N_5O_2S$ | 405 | 4 |
| 78 | 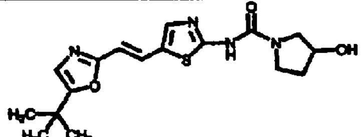 | $C_{17}H_{22}N_4O_3S$ | 363 | 4 |
| 79 | 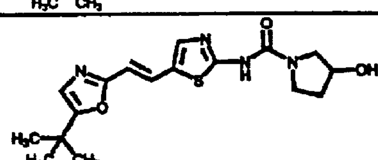 | $C_{18}H_{25}N_5O_2S$ | 377 | 4 |
| 80 | 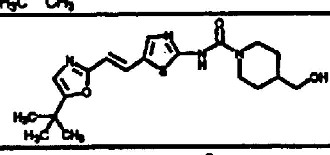 | $C_{19}H_{26}N_4O_3S$ | 392 | 4 |
| 81 | 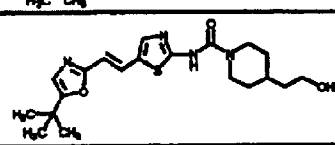 | $C_{20}H_{28}N_4O_3S$ | 406 | 4 |

Figure 9

| Example | Structure | Molecular Formula | MS (M+H)+ | Procedure of Example |
|---|---|---|---|---|
| 82 | 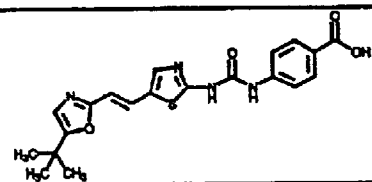 | $C_{20}H_{20}N_4O_4S$ | 413 | 4 |
| 83 | 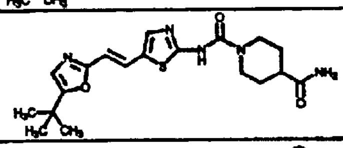 | $C_{19}H_{25}N_5O_3S$ | 405 | 4 |
| 84 | 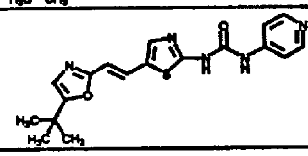 | $C_{18}H_{19}N_5O_2S$ | 370 | 4 |
| 85 | 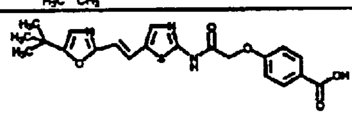 | $C_{21}H_{21}N_3O_5S$ | 428 | 4 |
| 86 | 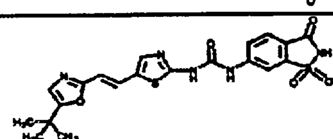 | $C_{20}H_{19}N_5O_5S_2$ | 475 | 4 |
| 87 | 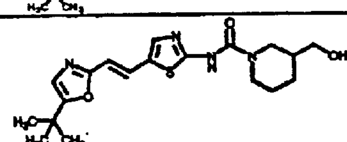 | $C_{19}H_{26}N_4O_3S$ | 392 | 4 |
| 88 | 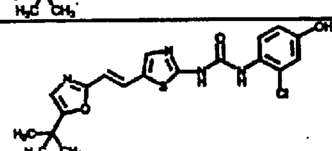 | $C_{19}H_{19}ClN_4O_3S$ | 420 | 4 |
| 89 | 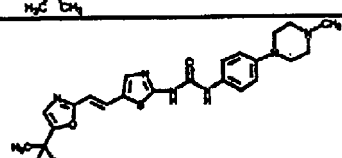 | $C_{24}H_{30}N_6O_2S$ | 468 | 4 |
| 90 | 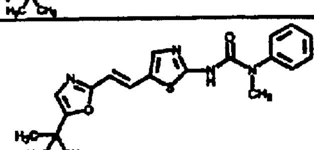 | $C_{20}H_{22}N_4O_2S$ | 383 | 4 |

Figure 10

| Example | Structure | Molecular Formula | MS (M+H)+ | Procedure of Example |
|---|---|---|---|---|
| 91 | 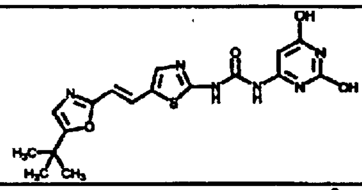 | C17H18N6O4S | 403 | 4 |
| 92 | 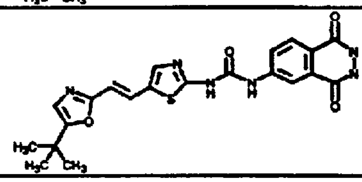 | C21H20N6O4S | 454 | 4 |
| 93 | 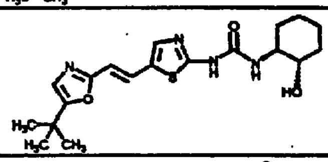 | C19H26N4O3S | 392 | 4 |
| 94 | 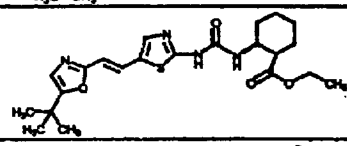 | C22H30N4O4S | 448 | 4 |
| 95 | 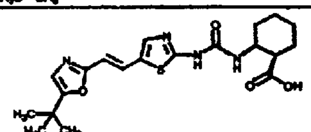 | C20H26N4O4S | 420 | 4 |
| 96 | 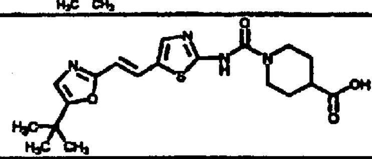 | C19H24N4O4S | 405 | 4 |
| 97 | 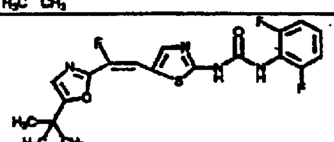 | C19H17F3N4O2S | 423 | 4 |
| 98 | 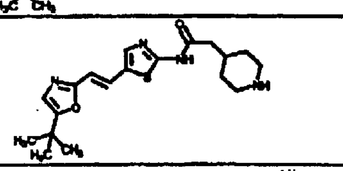 | C19H26N4O2S | 376 | 4 |
| 99 | 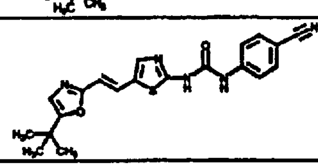 | C20H19N5O2S | 394 | 4 |

Figure 11

| Example | Structure | Molecular Formula | MS (M+H)+ | Procedure of Example |
|---|---|---|---|---|
| 100 | 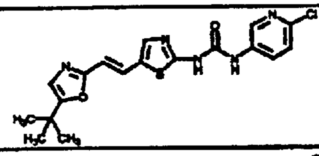 | C18H18ClN5O2S | 405 | 4 |
| 101 | 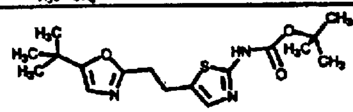 | C17H25N3O3S | 352 | 3 |
| 102 | 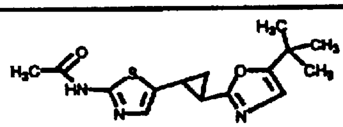 | C15H19N3O2S | 306 | Scheme 2 |
| 103 | 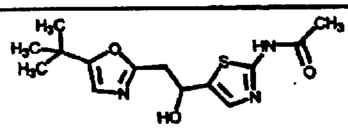 | C14H19N3O3S | 310 | Scheme 3 |
| 104 | 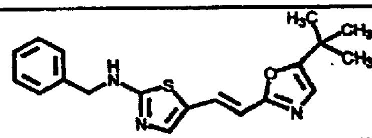 | C18H20N4OS | 341 | 6 |
| 105 | 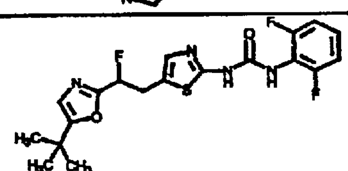 | C19H19F3N4O2S | 425 | 3 |
| 106 | 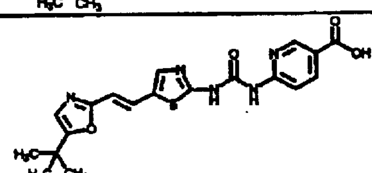 | C19H19N5O4S | 414 | 4 |
| 107 | 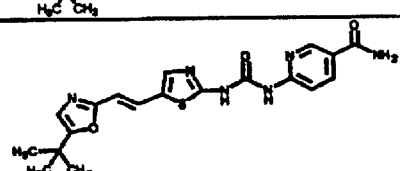 | C19H20N6O3S | 413 | 4 |
| 108 | 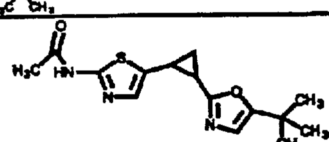 | C15H19N3O2S | 306 | Scheme 2 |
| 109 | 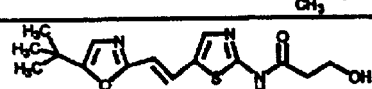 | C15H19N3O3S | 322 | 4 |

Figure 12

| Example | Structure | Molecular Formula | MS (M+H)+ | Procedure of Example |
|---|---|---|---|---|
| 110 | 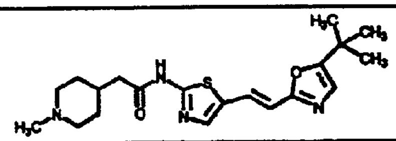 | C20 H28 N4 O2 S | 390 | 4 |
| 111 | 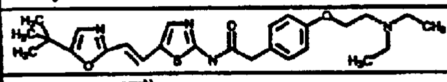 | C26 H34 N4 O3 S | 484 | 4 |
| 112 | 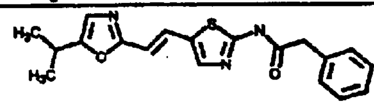 | C19 H19 N3 O2 S | 354 | 4 |
| 113 | 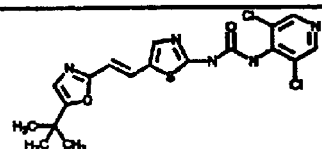 | C18 H17 Cl2 N5 O2 S | 439 | 4 |
| 114 | 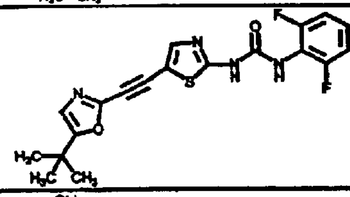 | C19 H16 F2 N4 O2 S | 403 | 5 |
| 115 | 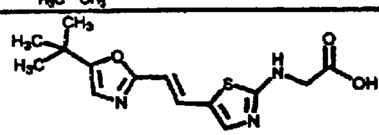 | C14 H17 N3 O3 S | 308 | 6 |
| 116 | 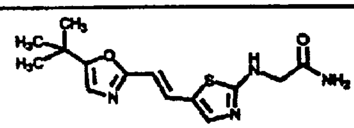 | C14 H18 N4 O2 S | 307 | 6 |
| 117 | 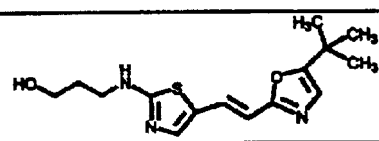 | C15 H21 N3 O2 S | 308 | 6 |
| 118 | 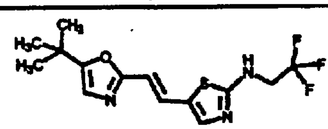 | C14 H16 F3 N3 O S | 332 | 6 |
| 119 | 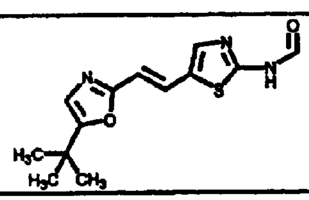 | C13 H15 N3 O2 S | 278 | 4 |

Figure 13

| Example | Structure | Molecular Formula | MS (M+H)+ | Procedure of Example |
|---|---|---|---|---|
| 120 | 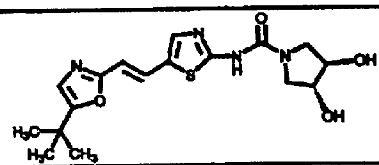 | $C_{17}H_{22}N_4O_4S$ | 379 | 4 |
| 121 | 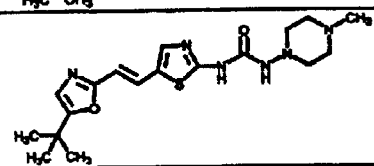 | $C_{18}H_{26}N_6O_2S$ | 392 | 4 |
| 122 | 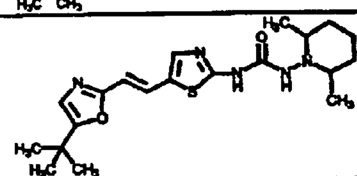 | $C_{20}H_{29}N_5O_2S$ | 405 | 4 |
| 123 | 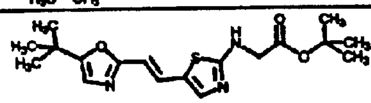 | $C_{18}H_{25}N_3O_3S$ | 364 | 6 |
| 124 | 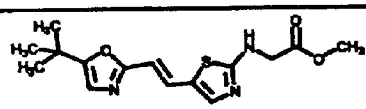 | $C_{15}H_{19}N_3O_3S$ | 322 | 6 |
| 125 | 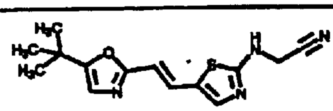 | $C_{14}H_{16}N_4OS$ | 289 | 6 |
| 126 | 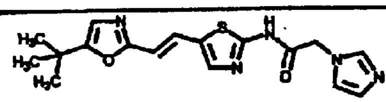 | $C_{17}H_{19}N_5O_2S$ | 358 | 4 |
| 127 | 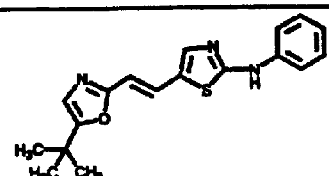 | $C_{18}H_{19}N_3OS$ | 326 | 6 |
| 128 | 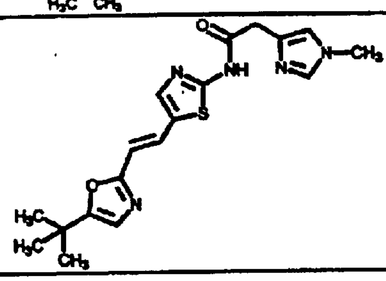 | $C_{18}H_{21}N_5O_2S$ | 372 | 4 |

Figure 14

| Example | Structure | Molecular Formula | MS (M+H)+ | Procedure of Example |
|---|---|---|---|---|
| 129 | 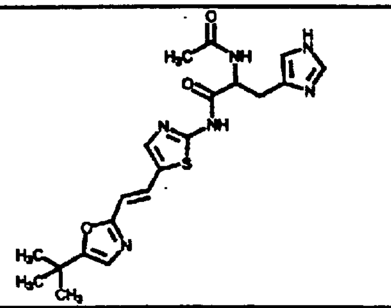 | C20H24N6O3S | 430 | 4 |
| 130 | 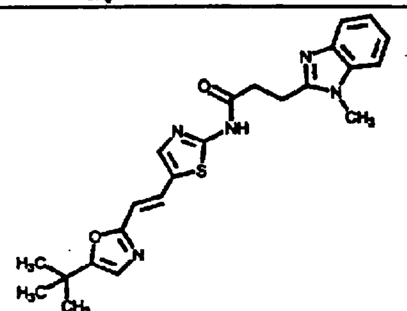 | C23H25N5O2S | 437 | 4 |
| 131 | 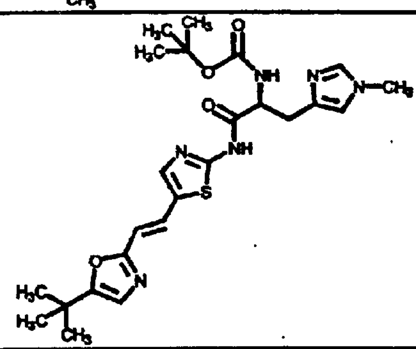 | C24H32N6O4S | 502 | 4 |
| 132 | 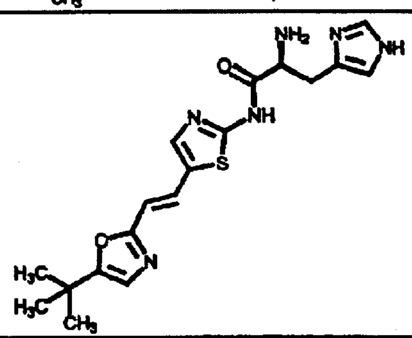 | C18H22N6O2S | 387 | 4 |

Figure 15

| Example | Structure | Molecular Formula | MS (M+H)+ | Procedure of Example |
|---|---|---|---|---|
| 133 | 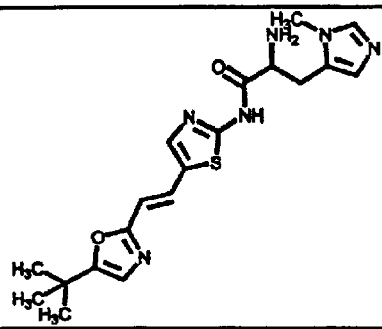 | $C_{19}H_{24}N_6O_2S$ | 402 | 4 |
| 134 | 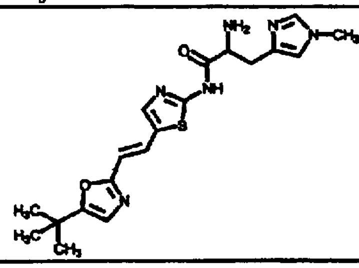 | $C_{19}H_{24}N_6O_2S$ | 402 | 4 |
| 135 | 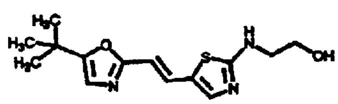 | $C_{14}H_{19}N_3O_2S$ | 294 | 6 |
| 136 | 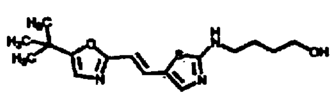 | $C_{16}H_{23}N_3O_2S$ | 322 | 6 |
| 137 | 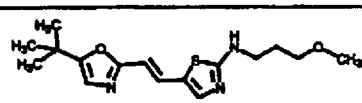 | $C_{16}H_{23}N_3O_2S$ | 322 | 6 |
| 138 | 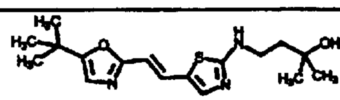 | $C_{17}H_{25}N_3O_2S$ | 336 | 6 |
| 139 | 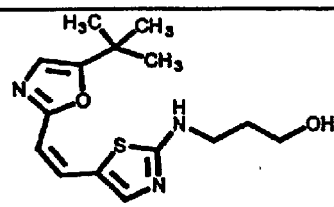 | $C_{15}H_{21}N_3O_2S$ | 308 | 6 |
| 140 | 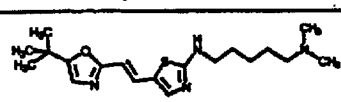 | $C_{19}H_{30}N_4OS$ | 364 | 6 |

Figure 16

| Example | Structure | Molecular Formula | MS (M+H)+ | Procedure of Example |
|---|---|---|---|---|
| 141 | 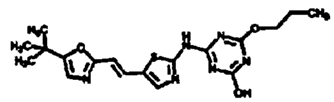 | $C_{18}H_{22}N_6O_3S$ | 403 | 6 |
| 142 | 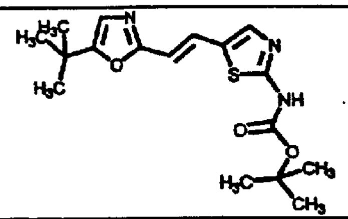 | $C_{17}H_{23}N_3O_3S$ | 350 | 4 |
| 143 | 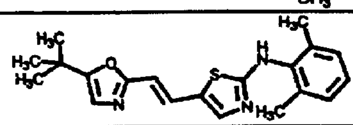 | $C_{20}H_{23}N_3OS$ | 354 | 6 |
| 144 | 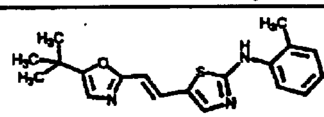 | $C_{19}H_{21}N_3OS$ | 340 | 6 |
| 145 | 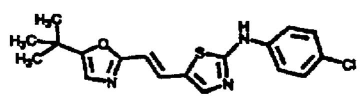 | $C_{18}H_{18}ClN_3OS$ | 361 | 6 |
| 146 | 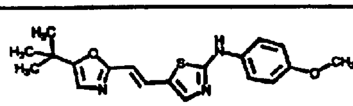 | $C_{19}H_{21}N_3O_2S$ | 356 | 6 |
| 147 | 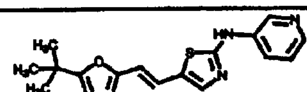 | $C_{17}H_{18}N_4OS$ | 327 | 6 |
| 148 | 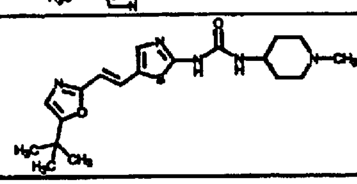 | $C_{19}H_{27}N_5O_2S$ | 391 | 4 |
| 149 | 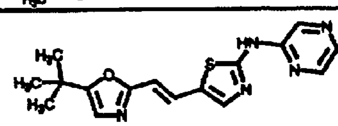 | $C_{16}H_{17}N_5OS$ | 328 | 6 |
| 150 | 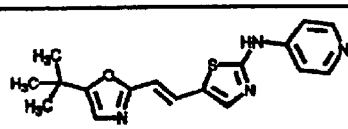 | $C_{17}H_{18}N_4OS$ | 327 | 6 |

Figure 17

| Example | Structure | Molecular Formula | MS (M+H)+ | Procedure of Example |
|---|---|---|---|---|
| 151 | 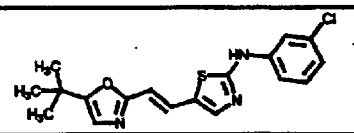 | C18H18ClN3OS | 361 | 6 |
| 152 | 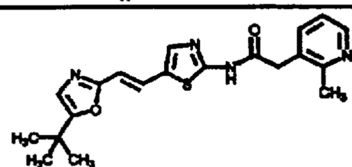 | C20H22N4O2S | 383 | 4 |
| 153 | 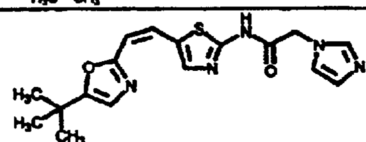 | C17H19N5O2S | 358 | 4 |
| 154 | 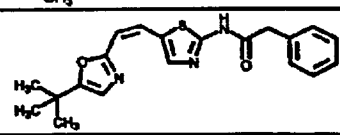 | C20H21N3O2S | 368 | 4 |
| 155 | 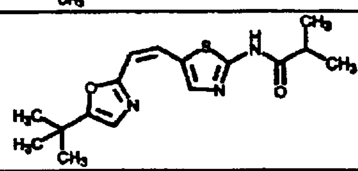 | C16H21N3O2S | 320 | 4 |
| 156 | 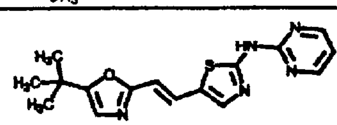 | C16H17N5OS | 328 | 6 |
| 157 | 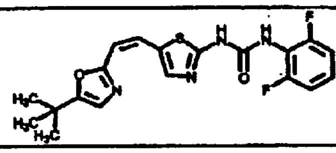 | C19H18F2N4O2S | 405 | 4 |
| 158 | 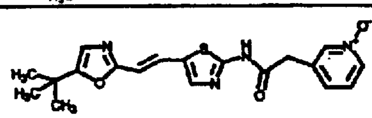 | C19H20N4O3S | 385 | 4 |
| 159 | 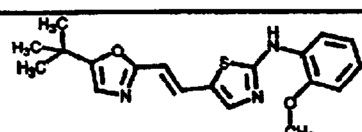 | C19H21N3O2S | 356 | 6 |
| 160 | 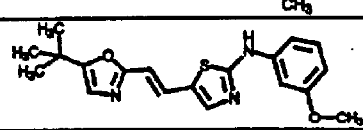 | C19H21N3O2S | 356 | 6 |

Figure 18

| Example | Structure | Molecular Formula | MS (M+H)+ | Procedure of Example |
|---|---|---|---|---|
| 161 | 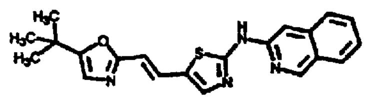 | $C_{21}H_{20}N_4OS$ | 377 | 6 |
| 162 | 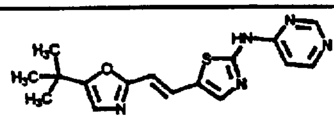 | $C_{16}H_{17}N_5OS$ | 328 | 6 |
| 163 | 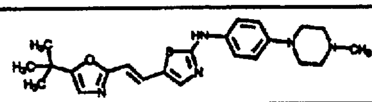 | $C_{23}H_{29}N_5OS$ | 425 | 6 |
| 164 | 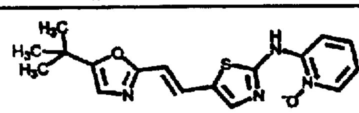 | $C_{17}H_{18}N_4O_2S$ | 343 | 6 |
| 165 | 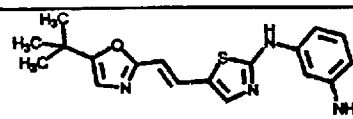 | $C_{18}H_{20}N_4OS$ | 341 | 6 |
| 166 | 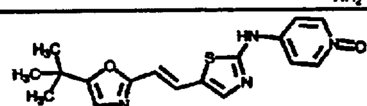 | $C_{17}H_{18}N_4O_2S$ | 343 | 6 |
| 167 | 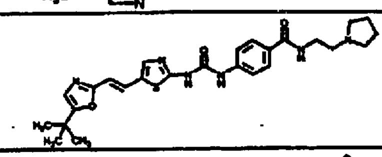 | $C_{26}H_{32}N_6O_3S$ | 510 | 4 |
| 168 | 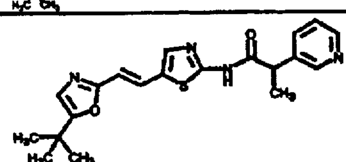 | $C_{20}H_{22}N_4O_2S$ | 383 | 4 |
| 169 | 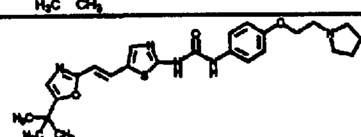 | $C_{25}H_{31}N_5O_3S$ | 483 | 4 |
| 170 | 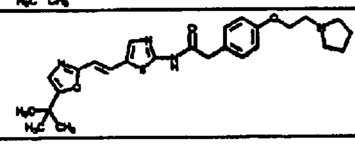 | $C_{26}H_{32}N_4O_3S$ | 482 | 4 |
| 171 | 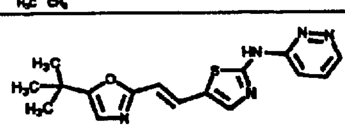 | $C_{16}H_{17}N_5OS$ | 328 | 6 |

Figure 19

| Example | Structure | Molecular Formula | MS (M+H)+ | Procedure of Example |
|---|---|---|---|---|
| 172 | 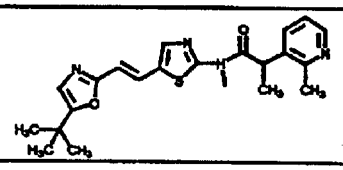 | C21 H24 N4 O2 S | 398 | 4 |
| 173 | 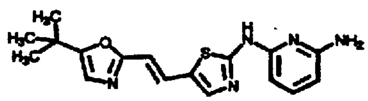 | C17 H19 N5 O S | 342 | 6 |
| 174 | 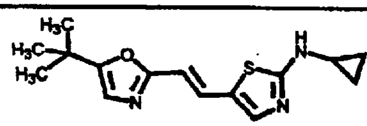 | C15 H19 N3 O S | 290 | 6 |
| 175 | 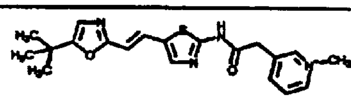 | C20 H23 N4 O2 S | 385 | 4 |
| 176 | 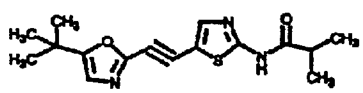 | C16 H19 N3 O2 S | 318 | 5 |
| 177 | 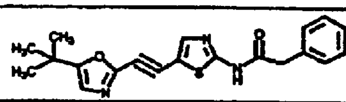 | C20 H19 N3 O2 S | 366 | 5 |
| 178 | 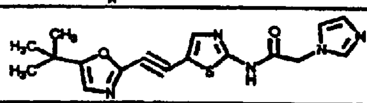 | C17 H17 N5 O2 S | 356 | 5 |
| 179 | 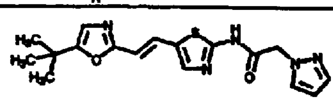 | C17 H19 N5 O2 S | 358 | 4 |
| 180 | 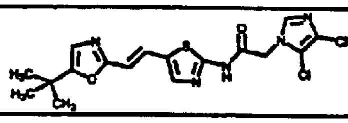 | C17 H17 Cl2 N5 O2 S | 427 | 4 |
| 181 | 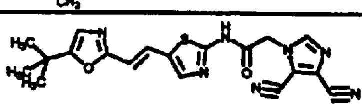 | C19 H17 N7 O2 S | 408 | 4 |
| 182 | 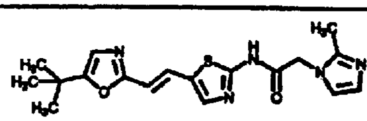 | C18 H21 N5 O2 S | 372 | 4 |
| 183 | 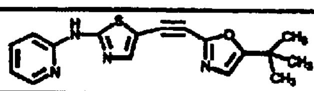 | C17 H16 N4 O S | 325 | 5 |

Figure 20

| Example | Structure | Molecular Formula | MS (M+H)$^+$ | Procedure of Example |
|---|---|---|---|---|
| 184 | 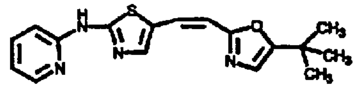 | $C_{17}H_{18}N_4OS$ | 327 | 6 |
| 185 | 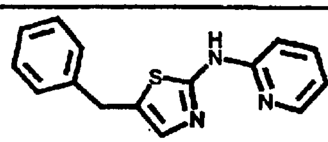 | $C_{15}H_{13}N_3S$ | 268 | 6 |
| 186 | 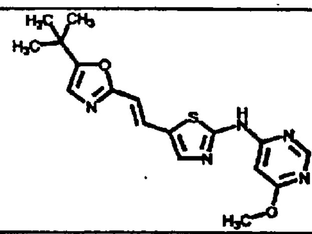 | $C_{17}H_{19}N_5O_2S$ | 358 | 6 |
| 187 | 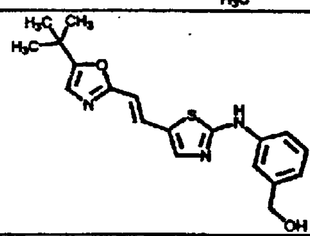 | $C_{19}H_{21}N_3O_2S$ | 356 | 6 |
| 188 | 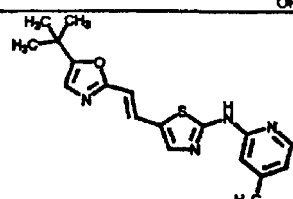 | $C_{18}H_{20}N_4OS$ | 341 | 6 |
| 189 | 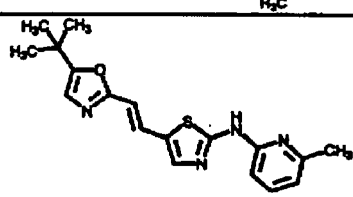 | $C_{18}H_{20}N_4OS$ | 341 | 6 |

CARBON SUBSTITUTED AMINOTHIAZOLE INHIBITORS OF CYCLIN DEPENDENT KINASES

This patent application is a divisional application of U.S. Application Ser. No. 09/329,616, filed on Jun. 10, 1999, now U.S. Pat. No. 6,407,124, which claims priority benefit of U.S. Provisional Application No. 60/089,747, filed Jun. 18, 1998, the entire contents of which are herein incorporated by reference.

BRIEF DESCRIPTION OF THE INVENTION

The present invention is directed to compounds of the formula

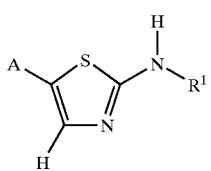

(I)

and pharmaceutically acceptable salts thereof. As used in formula I, and throughout the specification, the symbols have the following meanings:

$R^1 = R^2$, $COR^3$, $CONH_2$, $CONR^2R^3$, $COOR^2$, or $SO_2R^2$;

$R^2$ = alkyl, cycloalkyl, heterocycloalkyl, cycloalkylalkyl, heterocycloalkylalkyl, aryl, heteroaryl, arylalkyl, heteroarylalkyl;

$R^3$ = H, alkyl, cycloalkyl, heterocycloalkyl, cycloalkylalkyl, heterocycloalkylalkyl, aryl, heteroaryl, arylalkyl, heteroarylalkyl;

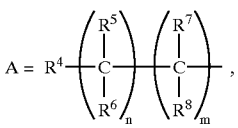

where n=0,1,2; m=1,2 but both n and m cannot be 2, or

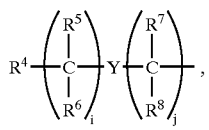

where i, j=0 or 1 but cannot both be 1, and Y=optionally substituted alkene, alkyne, or any 2 adjacent carbon atoms of a cycloalkyl or cycloheteroalkyl ring of 3–7 atoms;

$R^4$ = alkyl with two or more carbon atoms, cycloalkyl, heterocycloalkyl, cycloalkylalkyl, heterocycloalkylalkyl, aryl, heteroaryl, arylalkyl, heteroarylalkyl, or $R^9$, with the proviso that when $R^1$ is acetyl or propionyl and Y=alkene, then $R^4$ cannot be nitrofuryl or 2-quinolinyl;

$R^5$, $R^6$, $R^7$, $R^8$ = independently H, alkyl, cycloalkyl, heterocycloalkyl, cycloalkylalkyl, heterocycloalkylalkyl, aryl, heteroaryl, arylalkyl, heteroarylalkyl, halo, or hydroxy, alkoxy, amino, $NR^{12}R^{13}$, thio, or alkylthio, with the proviso that only one such heteroatom group is bonded to any one carbon atom;

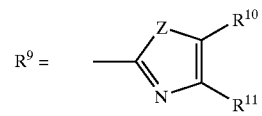

where Z=O, $NR^{14}$, S;

$R^{10}$, $R^{11}$ = independently H, alkyl, cycloalkyl, heterocycloalkyl, cycloalkylalkyl, heterocycloalkylalkyl, aryl, heteroaryl, arylalkyl, heteroarylalkyl, halo, hydroxy, alkoxy, alkylcarbonyloxy, carboxy, alkyloxycarbonyl, amino, $NR^{15}R^{16}$, carbamoyl, ureido, thio, or alkylthio;

$R^{12}$, $R^{13}$, $R^{14}$, $R^{15}$, $R^{16}$ = independently H, alkyl, cycloalkyl, heterocycloalkyl, cycloalkylalkyl, heterocycloalkylalkyl, aryl, heteroaryl, arylalkyl, or heteroarylalkyl.

The compounds of formula I are protein kinase inhibitors and are useful in the treatment of proliferative diseases, for example, cancer, inflammation and arthritis. They may also be useful in the treatment of Alzheimer's disease, and cardiovascular disease.

DESCRIPTION OF THE INVENTION

The present invention provides for compounds of formula I, pharmaceutical compositions employing such compounds, and for methods of using such compounds.

Listed below are definitions of various terms used to describe the compounds of the instant invention. These definitions apply to the terms as they are used throughout the specification (unless they are otherwise limited in specific instances) either individually or as part of a larger group.

It should be noted that any heteroatom with unsatisfied valances is assumed to have the hydrogen atom to satisfy the valances.

Carboxylate anion refers to a negatively charged group —COO⁻.

The term "alkyl" or "alk" refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), alkyloxycarbonyl (—COOR), alkylcarbonyloxy (—OCOR), amino (—$NH_2$), carbamoyl (—NHCOOR— or —OCONHR—), urea (—NHCONHR—), amidinyl (—CNHNHR or —CNRNH₂), or thiol (—SH). Alkyl groups as defined may also comprise one or more carbon to carbon double bonds or one or more carbon to carbon triple bonds.

The term "alkenyl" refers to a hydrocarbon radical straight, branched or cyclic containing from 2 to 12 carbon atoms and at least one carbon to carbon double bond.

The term "alkynyl" refers to a hydrocarbon radical straight, branched or cyclic containing from 2 to 12 carbon atoms and at least one carbon to carbon triple bond.

Cycloalkyl is a specie of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, etc. Exemplary substituents include one or more of the following groups: halogen, alkyl, alkoxy, alkyl hydroxy, amino, nitro, cyano, thiol and/or alkylthio.

The terms "alkoxy" or "alkylthio", as used herein, denote an alkyl group as described above bonded through an oxygen linkage (—O—) or a sulfur linkage (—S—), respectively.

Sulfoxide and sulfone denote groups bonded by —SO— or —$SO_2$— linkages, respectively.

The term "alkyloxycarbonyl", as used herein, denotes an alkoxy group bonded through a carbonyl group. An alkoxycarbonyl radical is represented by the formula: —C(O)OR, where the R group is a straight or branched $C_{1-6}$ alkyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

The term "arylalkyl", as used herein, denotes an aromatic ring bonded to an alkyl group as described above.

The term "aryl" refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, trifluoromethyl, amino, cycloalkyl, cyano, alkyl $S(O)_m$ (m=, 0,1, 2), or thiol.

The term "heteroaryl" refers to a monocyclic aromatic hydrocarbon group having 5 or 6 ring atoms, or a bicyclic aromatic group having 8 to 10 atoms, containing at least one heteroatom, O, S, or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Exemplary heteroaryl groups include the following: thienyl, furyl, pyrrolyl, pyridinyl, imidazolyl, pyrrolidinyl, piperidinyl, thiazolyl, oxazolyl, triazolyl, pyrazolyl, isoxazolyl, isothiazolyl, pyrazinyl, tetrazolyl, pyridazinyl, pyrimidinal, triazinylazepinyl, indolyl, isoindolyl, quinolinyl, isoquinolinyl, benzothiazolyl, benzoxazolyl, benzimidazolyl, benzoxadiazolyl, benzofurazanyl and tetrahydropyranyl. Exemplary substituents include one or more of the following: halogen, alkyl, alkoxy, hydroxy, carboxy, carbamoyl, alkyloxycarbonyl, trifluoromethyl, cycloalkyl, nitro, cyano, amino, alkylS(O)$_m$ (m=, 0,1, 2), or thiol.

The term "heteroarylium" refers to heteroaryl groups bearing a quaternary nitrogen atom and thus a positive charge.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by said heteroatoms.

The term "quaternary nitrogen" refers to a tetravalent positively charged nitrogen atom including, e.g. the positively charged nitrogen in a tetraalkylammonium group (e.g. tetramethylammonium, N-methylpyridinium), the positively charged nitrogen in protonated ammonium species (e.g. trimethylhydroammonium, N-hydropyridinium), the positively charged nitrogen in amine N-oxides (e.g. N-methylmorpholine-N-oxide, pyridine-N-oxide), and the positively charged nitrogen in an N-amino-ammonium group (e.g. N-aminopyridinium).

The term "heteroatom" means O, S or N, selected on an independent basis.

The term "halogen" or "halo" refers to chlorine, bromine, fluorine or iodine.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

Suitable examples of salts of the compounds according to the invention with inorganic or organic acids are hydrochloride, hydrobromide, sulfate, phosphate. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

All configurational isomers of compounds of the present invention are contemplated, either in admixture or in pure or substantially pure form. The definition of compounds of the present invention very particularly embraces both cis (Z) and trans (E) alkene isomers, as well as cis and trans isomers of cycloalkyl or heterocycloalkyl rings.

It should be understood that solvates (e.g. hydrates) of the compounds of formula I are also within the scope of the present invention. Methods of salvation are generally known in the art. Accordingly, the compounds of the instant invention may be in the free or hydrate form, and may be obtained by methods exemplified by the following schemes.

The synthesis of compounds of formula I can proceed through the known aldehyde of formula II (Scheme 1) which was prepared according to the procedures set forth in *II Farmaco* 44, 1011, (1989) and the references therein. Treatment of II with either $(R^2CO)_2O$ or $R^1$—L, where L is a leaving group such as a halogen or sulfonate ester, yields compounds of formula III. Condensation of formula III with phosphorus-stabilized anions such as the phosphonate of formula IV or a Wittig reagent in the presence of base yields compounds of formula V (that is, compounds of formula I where A contains an alkene present as either the cis or trans isomer). Alternatively, compounds of formula V may be prepared by first reacting formula II with the phosphonate of formula IV or a Wittig reagent in the presence of base, and then treating the resulting product with $(R^2CO)_2O$ or $R^1$—L.

Scheme 1

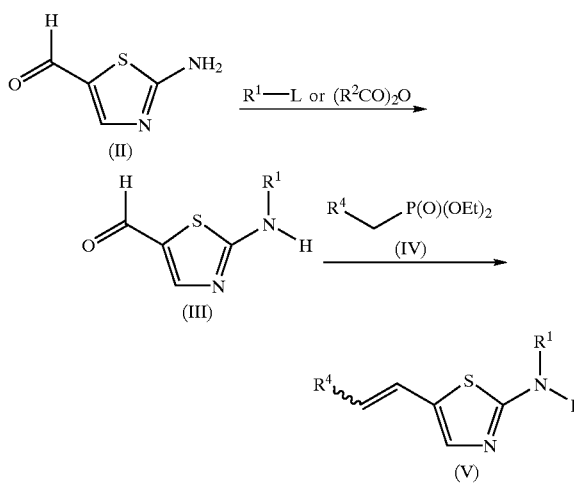

Compounds of formula V may be converted into other compounds of formula I as shown in Scheme 2. For example, treatment of compounds of formula V with agents such as H₂ on Pd/C yields the saturated compounds of formula VI (which is a compound of formula I. Alternatively compounds of formula V may be epoxidized with agents such as dimethyldioxirane or m-chloroperbenzoic acid to yield epoxides of formula VII (which are compounds of formula I where Y=the carbon atoms of oxirane). Cyclopropanation of the olefin with agents such as ZnCuCH₂ or diazomethane may yield cyclopropanes of formula VIII (which are compounds of formula I where Y=cyclopropane).

Scheme 2

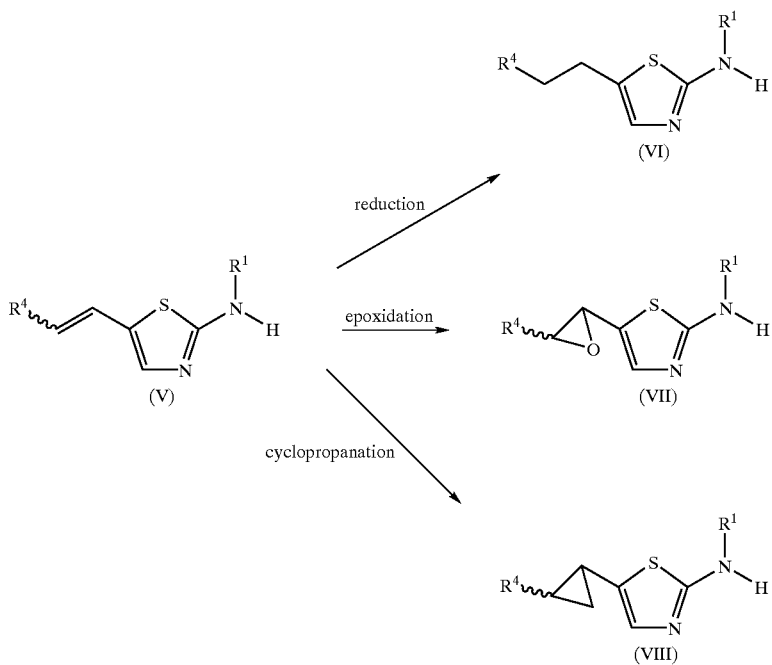

Aldehydes of formula III may also be converted into compounds of formula I which have $R^7$ or $R^8$ groups containing oxygen (Scheme 3). For example, addition of organometallic reagents of formula R*-M, where $R^*=R^4(R^5R^6C)_i$— or $R^4(R^5R^6C)_i$—Y— and M=a metal, would yield compounds of formula IX (that is, compounds of formula I where $R^7$=hydroxy and $R^8$=H). Alkylation of the hydroxyl group in compounds of formula IX using W—L, where W=alkyl, cycloalkyl, heterocycloalkyl, cycloalkylalkyl, heterocycloalkylalkyl, aryl, heteroaryl, arylalkyl, or heteroarylalkyl, and L is a leaving group such as a halogen or sulfonate ester, would yield ethers of formula X (that is, compounds of formula I with $R^7$=alkoxy).

Scheme 3

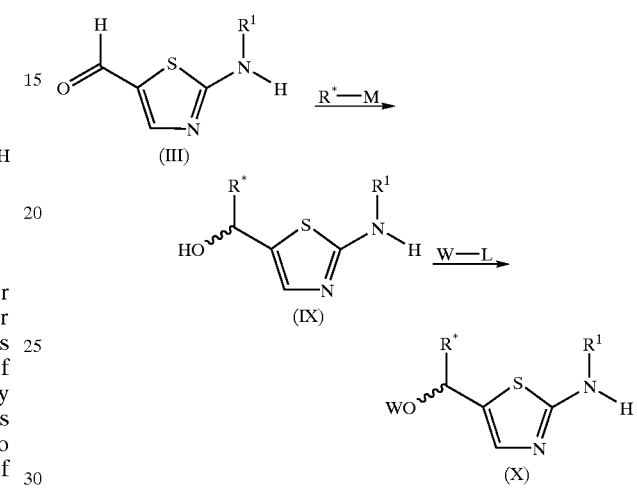

Scheme 4 outlines a procedure that may be used for the solid phase synthesis of compounds of formula I. A benzyl chloride resin, such as that depicted by formula XII, may be alkylated by an aminothiazole of formula III (where $R^1$=CF₃CO) to give a compound of formula XII. Coupling with phosphorus stabilized anions such as compounds of formula IV will yield alkenes of formula XIII which may be deprotected by a reducing agent such as sodium borohydride, or a base such as sodium hydroxide, to give amines of formula XIV. The amines of formula XIV may react with $R^1$—L or $(R^2CO)_2O$ to give compounds of formula XV, which may be cleaved from the resin with trifluoroacetic acid to give compounds of formula V (which are compounds of formula I where Y is an alkene). Compounds of formula IX or X may also be synthesized on solid phase using analogous chemistry to that shown in Scheme 3 by starting with aldehyde XII.

aldehydes may be reduced with agents such as sodium borohydride to give alcohols of formula XVI which may be converted into a compound of formula XVII, where L is a leaving group such as a halogen or sulfonate ester, by treatment with agents such as p-toluenesulfonyl chloride and base or thionyl chloride. The anion of dialkylmalonate esters of formula XVIII may be alkylated by compounds of formula XVII to form diesters of formula XIX, where W=alkyl, cycloalkyl, heterocycloalkyl, cycloalkylalkyl, heterocycloalkylalkyl, aryl, heteroaryl, arylalkyl, or heteroarylalkyl. These diesters may be saponified and decarboxylated to form acids of formula XX which may be coupled with amines of formula XXI to give amides of formula XXII. These amides may be cyclized upon exposure to dehydrating agents such as $POCl_3$ to form compounds of formula VI which are compounds of formula I where Z=O.

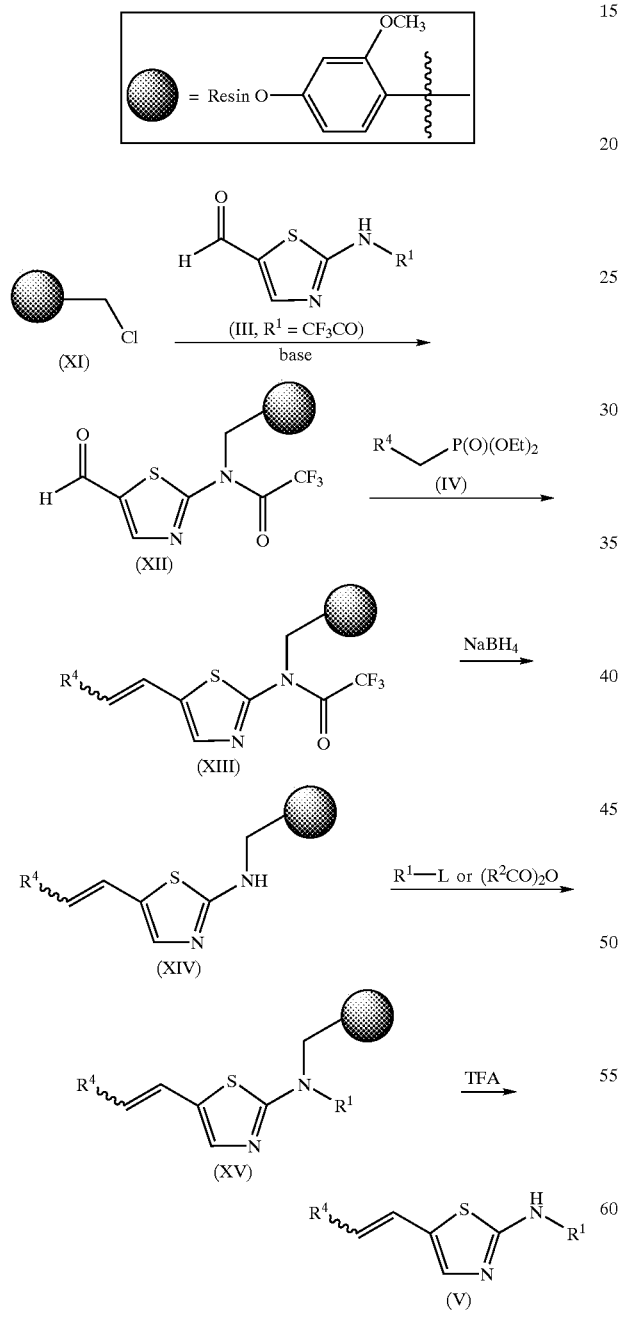

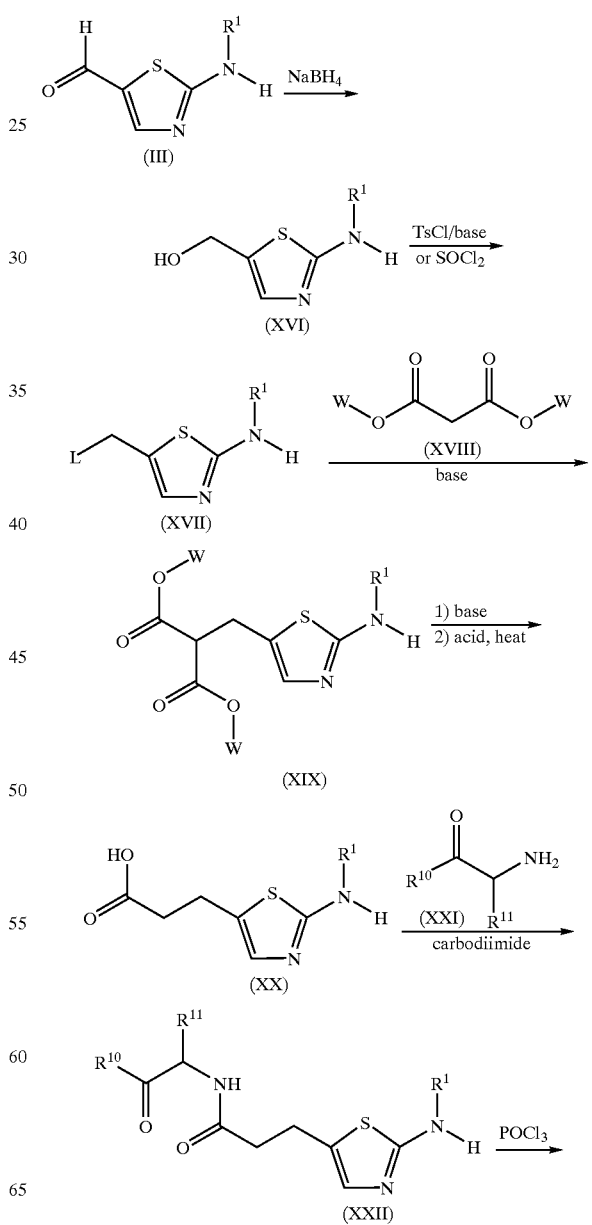

Compounds of formula I wherein $R^4=R^9$ may be synthesized from aldehydes of formula III (Scheme 5). These

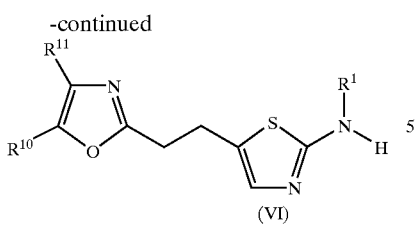

(VI)

Compounds of formula I wherein R4=R9 and Y=alkynyl or Z-alkenyl may be prepared from halomethyl oxazoles such as XXIII (Scheme 6). Displacement of the chlorine to give the acetate XXIV, followed by basic hydrolysis and oxidation provides a 2-oxazolyl aldehyde XXVI. The aldehyde may be treated with a reagent such as carbon tetrabromide and triphenylphosphine to give a dibromo olefin XXVII. Elimination of HBr by strong base, followed by lithiation and quenching the acetylenic anion with tributyltin chloride gives an acetylenic stannane XXVIII, which may be coupled with a 2-iodo aminothiazole XXIX, to give XXX, which is a compound of formula I wherein $R^4 = R^9$ and Y is alkynyl. The acetylenic compounds of formula XXX may be hydrogenated to provide cis olefins XXXI and XXXIII, which are compounds of formula I wherein $R^4 = R^9$ and Y is Z-alkenyl.

Scheme 6

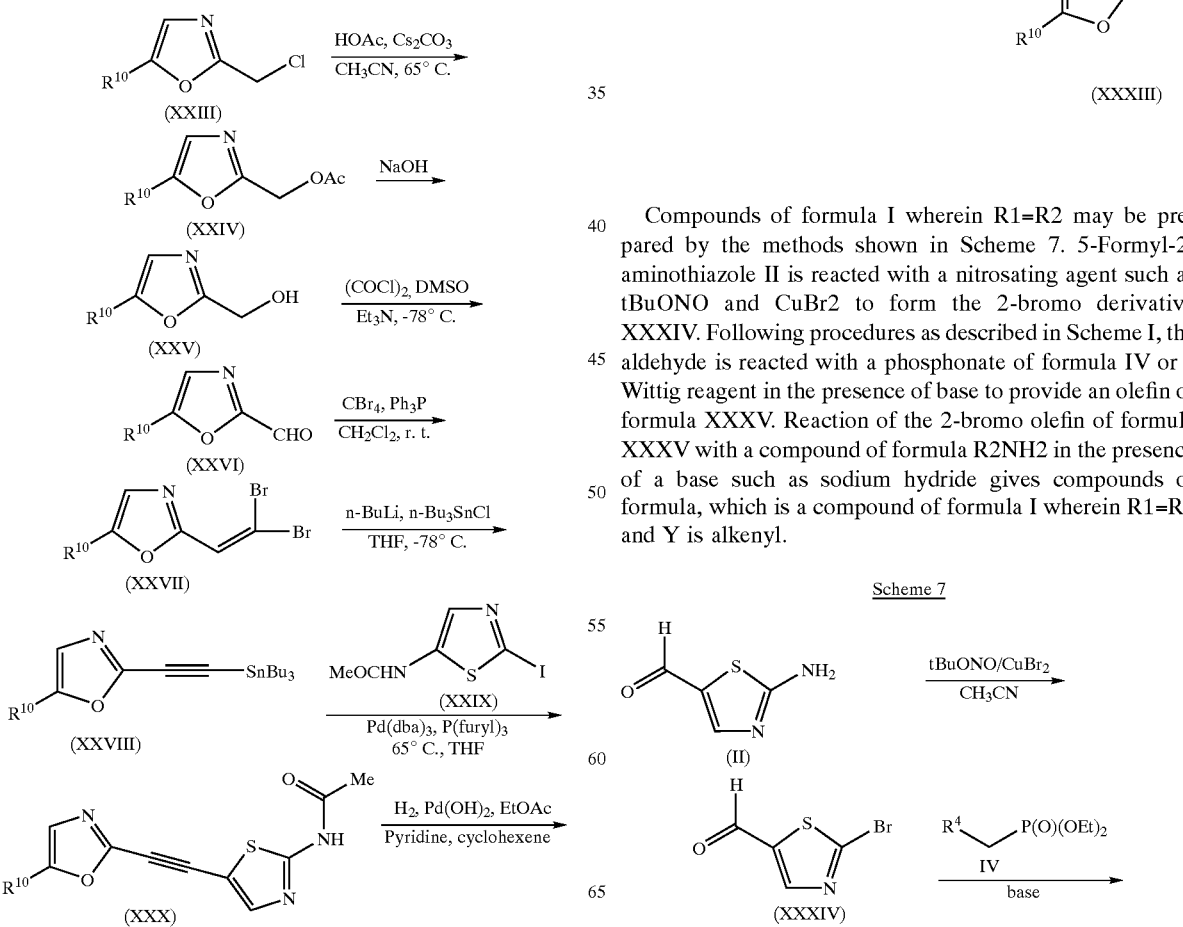

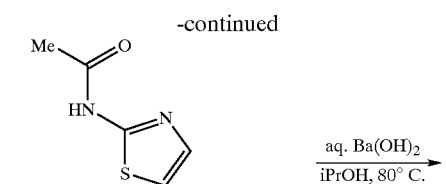

(XXXI)

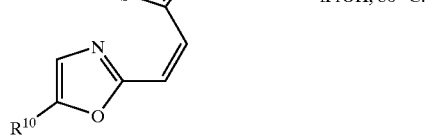

(XXXII)

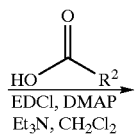

(XXXIII)

Compounds of formula I wherein R1=R2 may be prepared by the methods shown in Scheme 7. 5-Formyl-2-aminothiazole II is reacted with a nitrosating agent such as tBuONO and CuBr2 to form the 2-bromo derivative XXXIV. Following procedures as described in Scheme I, the aldehyde is reacted with a phosphonate of formula IV or a Wittig reagent in the presence of base to provide an olefin of formula XXXV. Reaction of the 2-bromo olefin of formula XXXV with a compound of formula R2NH2 in the presence of a base such as sodium hydride gives compounds of formula, which is a compound of formula I wherein R1=R2 and Y is alkenyl.

Scheme 7

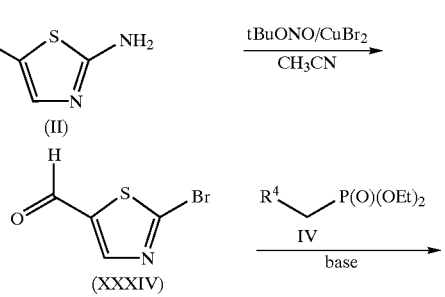

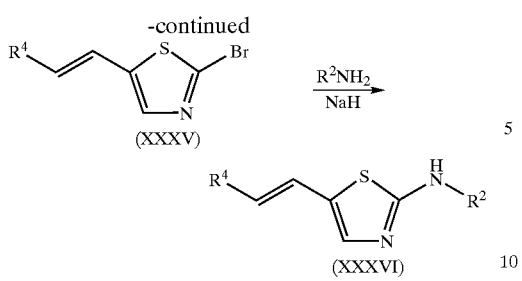

Alternatively, compounds of formula XXXVI where $R^1=R^2$ and Y is alkenyl may be prepared according to Scheme 8. The amino group of compound II may be protected with a reagent such as di-t-butyl dicarbonate to give XXXVII, followed by reaction with a phosphonate of formula IV or a Wittig reagent in the presence of base such as an alkoxide or sodium hydride to give a compound of formula XXXVIII. Treatment of XXXVIII with $R^2L$ where L is a leaving group such as halo or sulfonate, in the presence of base, followed by removal of the protecting group gives a compound of formula XXXVI, which is a compound of formula I where $R^1=R^2$ and Y is alkenyl.

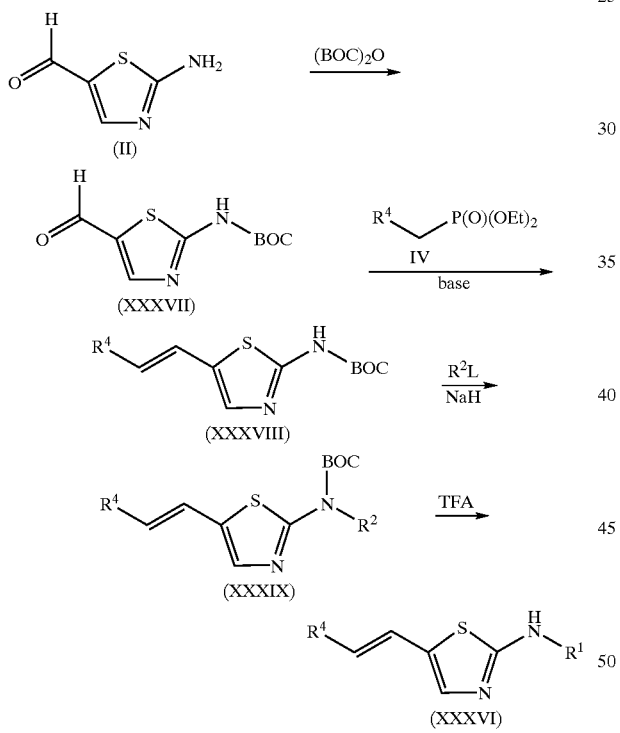

Compounds of formula $R^4CH_2P(O)(OEt)_2$ may be prepared from compounds of formula $R^4CH_2L$, where L is a leaving group such as halogen or sulfonate ester, by heating with triethylphosphite. Compounds of formula $R^9$-L, where Z=O, may be prepared from $LCH_2CN$ and $R^{11}C(N_2)COR^{10}$, according to part E of Example 2.

The starting compounds of Schemes 1–7 are commercially available or may be prepared by methods known to one of ordinary skill in the art.

All compounds of formula I may be prepared by modification of the procedures described herein.

Preferred compounds of formula I are those where:
$R^1=R^2$, $COR^3$, or $CONR^2R^3$;
$R^2$=alkyl, aryl, or heteroaryl;
$R^3$=H, alkyl, aryl, heteroaryl, arylalkyl, or heteroarylalkyl;

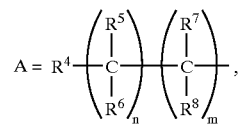

where n=0, 1, 2; m=1, 2, or

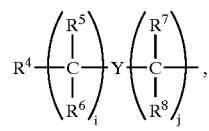

where i, j=0 or 1 but cannot both be 1, and Y=optionally substituted alkene, alkyne, or any two adjacent carbon atoms of a cycloalkyl ring;
$R^4$=alkyl with two or more carbon atoms, aryl, heteroaryl, or $R^9$;
$R^5$, $R^6$, $R^7$, $R^8$=independently H, or alkyl;

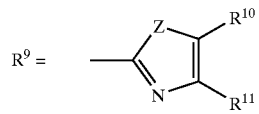

where Z=O;
$R^{10}$, $R^{11}$=independently H, or alkyl.

The compounds according to the invention have pharmacological properties; in particular, the compounds of formula I are inhibitors of protein kinases such as the cyclin dependent kinases (cdks), for example, cdc2 (cdk1), cdk2, and cdk4. The novel compounds of formula I are expected to be useful in the therapy of proliferative diseases such as cancer, inflammation, arthritis, Alzheimer's disease and cardiovascular disease. These compounds may also be useful in the treatment of topical and systemic fungal infections.

More specifically, the compounds of formula I are useful in the treatment of a variety of cancers, including (but not limited to) the following:
  carcinoma, including that of the bladder, breast, colon, kidney, liver, lung, ovary, pancreas, stomach, cervix, thyroid, prostate, and skin;
  hematopoietic tumors of lymphoid lineage, including acute lymphocytic leukemia, B-cell lymphoma, and Burkett's lymphoma;
  hematopoietic tumors of myeloid lineage, including acute and chronic myelogenous leukemias and promyelocytic leukemia;
  tumors of mesenchymal origin, including fibrosarcoma and rhabdomyosarcoma; and
  other tumors, including melanoma, seminoma, teratocarcinoma, osteosarcoma, neuroblastoma and glioma.

Due to the key role of cdks in the regulation of cellular proliferation in general, inhibitors could act as reversible cytostatic agents which may be useful in the treatment of any disease process which features abnormal cellular proliferation, e.g., neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, angiogenesis, and endotoxic shock.

Compounds of formula I may also be useful in the treatment of Alzheimer's disease, as suggested by the recent finding that cdk5 is involved in the phosphorylation of tau protein (*J. Biochem,* 117, 741–749 (1995)).

Compounds of formula I may also act as inhibitors of other protein kinases, e.g., protein kinase C, her2, rafl, MEK1, MAP kinase, EGF receptor, PDGF receptor, IGF receptor, Pl3 kinase, weel kinase, Src, Abl, and thus be effective in the treatment of diseases associated with other protein kinases.

The compounds of this invention may also be useful in combination with known anti-cancer treatments such as radiation therapy or with cytostatic and cytotoxic agents, such as for example, but not limited to, DNA interactive agents, such as cisplatin or doxorubicin; inhibitors of farnesyl protein transferase, such as those described in pending U.S. application Ser. No. 08/802,239 which was filed on Feb. 20, 1997; topoisomerase II inhibitors, such as etoposide; topoisomerase I inhibitors, such as CPT-11 or topotecan; tubulin stabilizing agents, such as paclitaxel, docetaxel or the epothilones; hormonal agents, such as tamoxifen; thymidilate synthase inhibitors, such as 5-fluorouracil; and antimetabolites, such as methoxtrexate; antiangiogenic agents, such as angiostatin; and kinase inhibitors, such as her2 specific antibodies.

If formulated as a fixed dose, such combination products employ the compounds of this invention within the dosage range described below and the other pharmaceutically active agent within its approved dosage range. For example, the cdc2 inhibitor olomucine has been found to act synergistically with known cytotoxic agents in inducing apoptosis (*J. Cell Sci.,* 108, 2897 (1995)). Compounds of formula I may be used sequentially with known anti-cancer or cytotoxic agents when a combination formulation is inappropriate.

cdc2/cyclin B1 Kinase Assay cdc2/cyclin B1 kinase activity was determined by monitoring the incorporation of $^{32}$P into histone HI. The reaction consisted of 50 ng baculovirus expressed GST-cdc2, 75 ng baculovirus expressed GST-cyclin B1, 1 μg histone HI (Boehringer Mannheim), 0.2 μCi of $^{32}$P γ-ATP and 25 μM ATP in kinase buffer (50 mM Tris, pH 8.0, 10 mM MgCl$_2$, 1 mM EGTA, 0.5 mM DWF). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., *J. of Cellular Biochemistry,* 45, 391–400 (1991), incorporated by reference herein).

cdk2/cyclin E Kinase Assay cdk2/cyclin E kinase activity was determined by monitoring the incorporation of $^{32}$P into the retinoblastoma protein. The reaction consisted of 2.5 ng baculovirus expressed GST-cdk2/cyclin E, 500 ng bacterially produced GST-retinoblastoma protein (aa 776–928), 0.2 μCi $^{32}$P γ-ATP and 25 μM ATP in kinase buffer (50 mM Hepes, pH 8.0, 10 mM MgCl$_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk 4/cyclin D1 Kinase Activity cdk4/cyclin D1 kinase activity was determined by monitoring the incorporation of $^{32}$P in to the retinoblastoma protein. The reaction consisted of 165 ng baculovirus expressed as GST-cdk4, 282 ng bacterially expressed as S-tag cyclin D1, 500 ng bacterially produced GST-retinoblastoma protein (aa 776–928), 0.2 μCi $^{32}$P γ-ATP and 25 μM ATP in kinase buffer (50 mM Hepes, pH 8.0, 10 mM MgCl$_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Coleman, K. G., Wautlet, B. S., Morissey, D, Mulheron, J. G., Sedman, S., Brinkley, P., Price, S., Wedster, K. R. (1997) Identification of CDK4 Sequences involved in cyclin D, and p16 binding. *J. Biol. Chem.* 272,30:18869–18874, incorporated by reference herein).

The following examples and preparations describe the manner and process of making and using the invention and are illustrative rather than limiting. It should be understood that there may be other embodiments which fall within the spirit and scope of the invention as defined by the claims appended hereto.

EXAMPLE 1

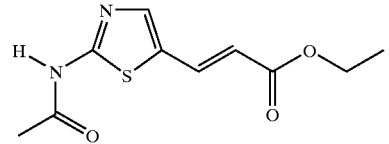

A. Preparation of 2-acetamido-5-bromothiazole

To a solution of 2-amino-5-bromothiazole (22.3 g, 85.9 mmol) in methylene chloride (100 mL) and pyridine (60 mL) was added acetic anhydride (11 mL) slowly with stirring. The mixture was allowed to stir for 2.5 hours, warmed to room temperature, and stirred for an additional 4 hours. Most of the solvent was removed in vacuo and the residue was washed with ethyl acetate and aqueous HCl. The organic solution was then washed with water, dried over MgSO$_4$ and concentrated to give a crude solid. This solid was triturated with Et$_2$O, filtered, washed with Et$_2$O, and dried to give 2-acetamido-5-bromothiazole as a solid (15.1 g, 80%, C$_5$H$_5$BrN$_2$OS, MS m/e 222 (M+H)$^+$).

B. Preparation of ethyl 3-((E)-2-acetamido-thiazol-5-yl)-acrylate

A mixture of acetamido-5-bromothiazole (440 mg, 2.0 mmol), ethyl acrylate (400 mg, 4 mmol) and triethylamine (3 mL) in DMF (3 mL) was stirred at 90° C. under argon in the presence of Pd(tol$_3$P)$_2$Cl$_2$ (150.0 mg) for 24 h. The mixture was concentrated and the residue was dissolved in methylene chloride (100 mL), washed with water and dried over MgSO$_4$. The solution was concentrated and the residue was purified by column chromatography (SiO$_2$, CH$_2$Cl$_2$:MeOH/100:5) to afford ethyl 3-((E)-2-acetamido-thiazol-5-yl)-acrylate (100 mg, 21%) as a solid (m.p. 239–240° C., C$_{10}$H$_{12}$N$_2$O$_3$S, MS m/e 240.9 (M+H)$^+$).

EXAMPLE 2

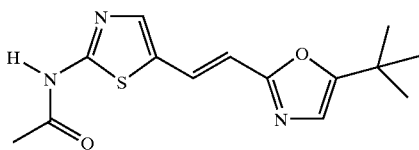

A. Preparation of 2-amino-thiazol-5-ylcarboxaldehyde

2-Amino-thiazol-5-ylcarboxaldehyde was synthesized according to the procedure set forth in *Il Farmaco* 44, 1011, (1989) and the references therein.

B. Preparation of 2-acetamido-thiazol-5-ylcarboxaldehyde

To a suspension of 2-amino-thiazol-5-ylcarboxaldehyde (5.0 g, 39 mmol) in toluene (500 mL) was added acetic anhydride (11.0 mL, 117 mmol). The mixture was heated to 110° C. for 5 hours. Upon cooling to room temperature, a solid precipitated out of the solution. The reaction mixture was concentrated under vacuum to give 2-acetamido-thiazol-5-ylcarboxaldehyde as a light brown colored solid (6.5 g, 98%, $C_6H_6N_2O_2S$, MS m/e 171 $(M+H)^+$).

C. Preparation of Diazomethane

Caution: diazomethane is potentially explosive. Care should be taken to use plastic containers, or glassware free of scratches. Solid KOH (60 g) was dissolved in water to make 150 mL of a 40% KOH solution. This solution was cooled at 0° C. and ether (500 mL) was added. To this cooled mixture was added 1-methyl-3-nitro-1-nitrosoguanidine (50 g, 0.34 mol) in portions over 45 minutes. After addition was complete, the ether layer was decanted and to give a solution of diazomethane which was used directly.

D. Preparation of 1-diazo-3,3-dimethyl-2-butanone

To the diazomethane solution was added a solution of trimethylacetyl chloride (15 mL, 0.12 mol) in ether (100 mL) dropwise over 40 minutes. After addition was complete, the solution was allowed to warm slowly overnight to room temperature. The solution was purged with a flow of nitrogen gas to remove any excess diazomethane and the resulting solution was concentrated to give 1-diazo-3,3-dimethyl-2-butanone as a yellow oil which was used directly in the next step.

E. Preparation of 2-(chloromethyl)-5-t-butyloxazole

To a stirred solution of chloroacetonitrile (40 mL) and boron trifluoride etherate (20 mL, 0.16 mmol) at 0° C. was added 1-diazo-3,3-dimethyl-2-butanone in chloroacetonitrile (40 mL) dropwise over a period of 20 minutes. After addition was complete, the mixture was stirred at 0° C. for one hour and then partitioned between saturated $NaHCO_3$, solution (700 mL) and $CH_2Cl_2$ (500 mL). The aqueous solution was extracted with $CH_2Cl_2$ (500 mL) and the combined organic layers were washed with brine (400 mL) and dried over $MgSO_4$. After filtration, the solution was concentrated and then distilled under vacuum using an oil bath temperature of 40° C. The 2-(chloromethyl)-5-t-butyloxazole (9.2 g, 44% overall from the acid chloride, $C_8H_{12}ClNO$, MS m/e 174 $(M+H)^+$) was obtained as a light yellow oil.

F. Preparation of (5-t-butyl-oxazol-2-ylmethyl)-phosphonic acid diethyl ester A solution of 2-(chloromethyl)-5-t-butyloxazole (8.00 g, 46.1 mmol) in triethylphosphite (15.3 g, 92.0 mmol) was heated at 120° C. for 18 hours. After cooling the mixture to room temperature, toluene (30 mL) was added and the solution was concentrated in vacuo with a bath temperature of 70° C. This procedure was repeated three times and the resulting brown oil was dried in vacuo at 90° C. for 30 minutes to give (5-t-butyl-oxazol-2-ylmethyl)-phosphonic acid diethyl ester (12.4 g, 98%, $C_{12}H_{22}NO_4P$, MS m/e 276 $(M+H)^+$) as a red-orange liquid.

G. Preparation of N-[(E)-5-(2-(5-t-butyl-oxazol-2-yl)-vinyl)-thiazol-2-yl]-acetamide To a solution of (5-butyl-oxazol-2-ylmethyl)-phosphonic acid diethyl ester (195 mg, 0.708 mmol) in tetrahydrofuran (10 mL) was added potassium t-butoxide (2.2 mL, 1 M in THF) via syringe. After 10 minutes, a solution of 2-acetamido-thiazo-5-ylcarboxaldehyde (100 mg, 0.587 mmol) in THF (6 mL) was added via syringe. Over the course of a half-hour, a precipitate formed in the solution. Methanol (1.5 mL) was added to dissolve the precipitate, and after an additional half-hour, the reaction was concentrated under reduced pressure to form a slurry. This was diluted with $CHCl_3$ (50 mL) and quenched with water (25 mL). The solution was extracted with $CHCl_3$ (3×50 mL) and ethyl acetate (3×50 mL) until all the formed solid was in solution. The combined organic layers were washed with water (50 mL) and dried over brine followed by $MgSO_4$ and then concentrated to give a yellow solid. The crude solid was purified by chromatography ($SiO_2$, 5% $MeOH/CHCl_3$) to afford N-[(E)-5-(2-(5-t-butyl-oxazol-2-yl)-vinyl)-thiazol-2-yl]-acetamide (118 mg, 69%, m.p. 275° C., $C_{14}H_{17}N_3O_2S$, MS m/e 292 $(M+H)^+$) as a light yellow solid. HPLC-HI 100% at 3.95 min (YMC S5 ODS coulm 4.6×50 mm, 10–90% aqueous methanol over 4 minutes containing 0.2% phosphoric acid, 4 mL/min, monitoring at 220 nm).

EXAMPLE 3

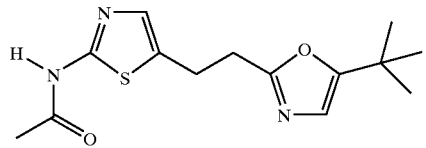

A. Preparation of N-[5-(2-(5-t-butyl-oxazol-2-yl)-ethyl)-thiazol-2-yl]-acetamide A solution N-[(E)-5-(2-(5-t-butyl-oxazol-2-yl)-vinyl)-thiazol-2-yl]acetamide (67 mg, 0.23 mmol) in ethyl acetate (10 mL) was added to a suspension of pre-reduced Pd/C (10%) in ethyl acetate (5 mL). The reaction flask was fitted with a hydrogen balloon and stirred for 24 hours. The reaction was filtered, and the mixture was resubmitted to hydrogenation using the same conditions as above. After an additional 24 hours, the reaction was filtered through a plug of celite, concentrated, and purified by chromatography ($SiO_2$, 5% $MeOH/CHCl_3$) to give N-[5-(2-(5-t-butyl-oxazol-2-yl)-ethyl)-thiazol-2-yl]-acetamide as a white solid (3.5 mg, 5%, $C_{14}H_{19}N_3O_2S$, MS m/e 294 $(M+H)^+$). HPLC-HI 91% at 6.75 min (Zorbax SB C18 column 4.6×75 mm, 10–90% aqueous methanol over 8 minutes containing 0.1% TFA, 2.5 mL/min, monitoring at 220 nm).

EXAMPLE 4

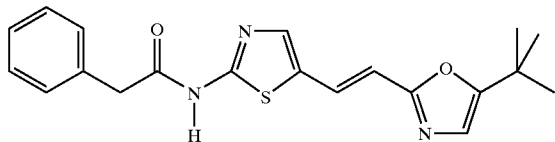

A. Preparation of [(E)-5-(2-(5-t-butyl-oxazol-2-yl)-vinyl)-thiazol-2-yl]-carbamic acid t-butyl ester A sample of [(E)-5-(2-(5-t-butyl-oxazol-2-yl)-vinyl)-thiazol-2-yl]-carbamic acid t-butyl ester could be prepared according to the methods described in Example 2.

B. Preparation of 2-amino-5-[(E)-2-(5-t-butyl-oxazol-2-yl)-vinyl]-thiazole

To a suspension of [5-(2-(5-t-butyl-oxazol-2-yl)-vinyl)-thiazo-2-yl]-carbamic acid t-butyl ester (1.5 g, 4.3 mmol) in tetrahydrofuran (30 mL) and water (3 mL) was added concentrated HCl (3 mL) dropwise. After addition was complete, the mixture was heated at 60° C. overnight. The solution was concentrated in vacuo to give a slurry, which was neutralized with saturated aqueous $NaHCO_3$ solution. The resulting solid was filtered and washed with water and dried to give the free base (732 mg, 68%, $C_{12}H_{15}N_3OS$, MS m/e 250 $(M+H)^+$).

C. Preparation of N-[5-(2-(5-t-butyl-oxazol-2-yl)-vinyl)-thiazol-2-yl]-phenylacetamide To a solution of 2-amino-5-[(E)-2-(5-t-butyl-oxazol-2-yl)-vinyl]-thiazole (20 mg, 0.08 mmol) in dry $CH_2Cl_2$ (1 mL) was added dry DMF (0.1 mL) and N,N-diisopropylethylamine (28 μL, 0.16 mmol). The resulting solution was cooled to 0° C. and phenyl acetyl chloride (21 μL, 0.16 mmol) was added via syringe. The reaction mixture was allowed to warm to room temperature over two hours and then concentrated. Chromatography ($SiO_2$, 5% MeOH/$CH_2Cl_2$) provided a N-[5-(2-(5-t-butyl-oxazol-2-yl)-vinyl)-thiazol-2-yl]-phenylacetamide as a mixture of Z and E isomers which were separated by reverse-phase HPLC to give the Z isomer (3 mg, 10%, MS m/e 368 $(M+H)^+$) as a light yellow solid, and the E isomer (3 mg, 10%, $C_{20}H_{21}N_3O_2S$, MS m/e 368 $(M+H)^+$) as a yellow solid. (Z)-isomer: HPLC-HI 86% at 4.05 min (YMC S5 ODS column 4.6×50 mm, 10–90% aqueous methanol over 4 minutes containing 0.1% TFA, 4 mL/min, monitoring at 254 nm). (E)-isomer: HPLC-HI 84% at 4.18 min (YMC S5 ODS column 4.6×50 mm, 10–90% aqueous methanol over 4 minutes containing 0.1% TFA, 4 mL/min, monitoring at 254 nm).

EXAMPLE 5

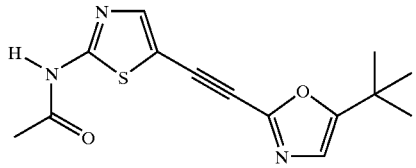

A. Preparation of 2-hydroxymethyl-5-t-butyloxazole

To a mixture of 2-chloromethyl-5-t-butyloxazole (13.0 g, 75.1 mmole), $Cs_2CO_3$ (36.0 g, 110.5 mmole) and acetic acid (10.5 mL, 192.6 mmole) in acetonitrile (120 ml) was heated at 65 deg C. overnight. All the solvent was removed under reduced pressure, the residue was partitioned between water (60 mL) and EtOAc (100 mL) and the aqueous layer was extracted with ethyl acetate (2×100 mL). The combined EtOAc solution was dried over $MgSO_4$ and concentrated to an oil.

The oil was dissolved in methanol (30 mL) and added with a solution of NaOH (6.50 g, 163 mmole) in 30 ml of water, and stirred at room temperature overnight. MeOH was removed under reduced pressure, and the aqueous layer was extracted with EtOAc (3×80 mL). The combined EtOAc solution was dried over $MgSO_4$ and concentrated to give 2-hydroxymethyl-5-t-butyloxazole as oil (11.76 g, 100%).

B. Preparation of 1,1-dibromo-2-(5'-t-butyloxazol-2-yl)ethylene

To a stirred solution of oxalyl chloride (45 mL, 90 mmole) at −78 deg C. under argon was added dropwise dimethyl sulfoxide (8.80 mL, 124 mmole). The reaction mixture was stirred at −78 deg C. for 10 min., and was treated with a solution of 2-hydroxymethyl-5-t-butyloxazole (11.7 g, 75.1 mmole) in anhydrous methylene chloride (30 mL) over 20 min. The mixture was stirred at this temperature for 1 hour, then triethylamine was added slowly (31.0 mL, 222 mmole), during which the reaction mixture became a yellowish slurry. After stirring at −78 deg C. for 20 min, the reaction mixture was warmed to room temperature, added with methylene chloride (100 mL) and stirred for 1 hour. The solid was filtered off and washed with EtOAc. The filtrate was washed with 5% aqueous citric acid (100 mL) and brine (50 mL), dried over $MgSO_4$. Concentration and column chromatography (silica gel, EtOAc/hexane 1:4) afforded 2-formyl-5-t-butyloxazole as a light yellow oil (10.1 g).

To a stirred solution of carbon tetrabromide (24.0 g, 72.4 mmole) in methylene chloride (200 mL) at 5–10 deg C. under argon atmosphere was added triphenylphosphine (37.0 g, 141 mmole) in portions. The reaction mixture was stirred for 5 min and treated with a solution of 2-formyl-5-t-butyloxazole in methylene chloride (60 mL). The reaction mixture was stirred at room temperature for 2 hours, while a white solid precipitated out of the solution. The solid was filtered off, the filtrate concentrated and purified (silica gel, EtOAc/hexane 1:4) to give 1,1-dibromo-2-(5-t-butyl-oxazol-2-yl)ethylene as a pale solid (9.13 g, 39%).

C. Preparation of N-[5-(2-(5-t-butyl-oxazol-2-yl)-acetelenyl)-thiazol-2-yl]-acetamide To a stirred solution of 1,1-dibromo-2-(5-t-butyl-oxazol-2-yl)ethylene (6.0 g, 19 mmole) in anhydrous THF (80 mL) at −78 deg C. under argon atmosphere. was added with 1.6 M n-butyllithium (32 mL, 51 mmole) in hexane dropwise over 20 min., the reaction mixture, stirred at −78 deg C. for 30 min and treated with tributyltin chloride (5.5 mL, 20 mmole). The reaction mixture was stirred for 30 min, warmed to 0 deg C., stirred at 0 deg C. for 30 min, and then at room temperature for 45 min. The mixture was passed through a short column of silica gel (deactivated with 2% triethylamine in hexane), and eluted with 10% EtOAc in dichloromethane to obtain crude product of 1-tributylstannyl-2-(5-t-butyl-oxazol-2-yl)acetylene as a brown oil (9.10 g).

To a stirred solution of above crude product of tin compound under argon and 2-N-acetylamino-5-iodothiazole (4.65 g, 17.3 mmole) in anhydrous THF (100 mL) at room temperature was added solid tris(dibenzylideneacetone)

dipalladium(0) (1.40 g, 1.53 mmole), followed by trifurylphosphine (2.0 g, 8.6 mmole). The reaction mixture was stirred at room temperature for 10 min., then heated at 65 deg C. for 2.5 hours. The catalyst was filtered off, the filtrate concentrated and purified by column silica gel chromatography (EtOAc/hexane 1:2 to 2:1) to give N-[5-(2-(5-t-butyl-oxazol-2-yl)-ethynyl)-thiazol-2-yl]-acetamide as a light brown solid (2.60 g, 46%). C14H15N3O2S, MS m/e 290 (M+H)+. HPLC-HI 100% at 4.02 min (YMC S5 ODS column 4.6×50 mm, 10–90% aqueous methanol over 4 minutes containing 0.2% phosphoric acid, 4 mL/min, monitoring at 220 nm).

EXAMPLE 6

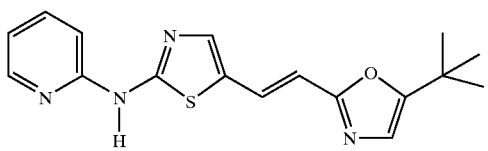

Preparation of N-[(E)-5-(2-(5-t-butyl-oxazol-2-yl)-vinyl)-thiazol-2-yl]-2-aminopyridine To a solution of 2-aminopyridine (238 mg, 2.56 mmol) in THF (8 mL) under argon was added sodium hydride (100 mg of 60% oil dispersion, 2.5 mmol) and the reaction stirred at 60 deg C. for 15 minutes, cooled to room temperature and 2-bromo-[(E)-5-(2-(5-t-butyl-oxazol-2-yl)-vinyl)-thiazole] (200 mg, 0.64 mmol) was added in one portion. The reaction mixture was stirred for 20 minutes, quenched with hydrochloric acid, washed with water and extracted with ethyl acetate. The organic layers were separated and concentrated to give a crude product which was heated with ethyl acetate: hexanes (1:1), cooled, filtered, and dried under vacuum to give the desired product. $C_{17}H_{18}N_4OS$, MS m/e 327 (M+H)$^+$. HPLC-HI 100% at 4.24 min (YMC S5 ODS column 4.6×50 mm, 10–90% aqueous methanol over 4 minutes containing 0.2% phosphoric acid, 4 mL/min, monitoring at 220 nm).

BRIEF DESCRIPTION OF DRAWINGS

Using the procedure described herein or by modification of the procedures described herein as known to one of ordinary skill in the art, additional compounds as shown in FIGS. 1–20 may be prepared.

Figure 2:
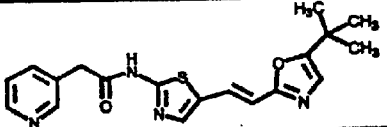
Figure 2:
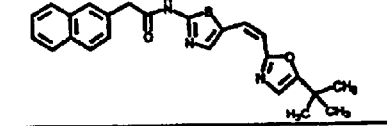
Figure 2:
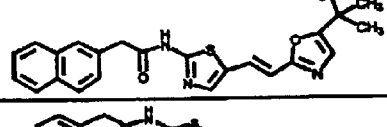
Figure 2:
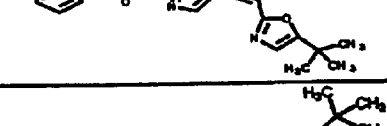
Figure 2:
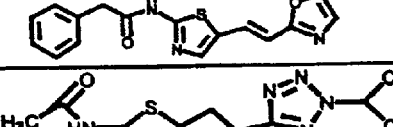
Figure 2:
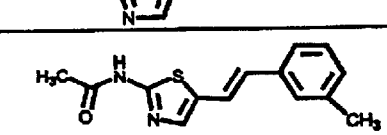
Figure 2:
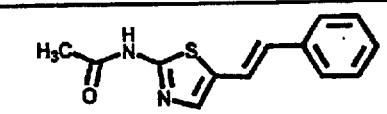
Figure 2:
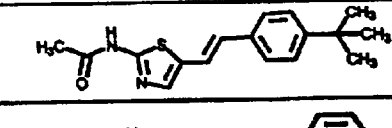
Figure 2:
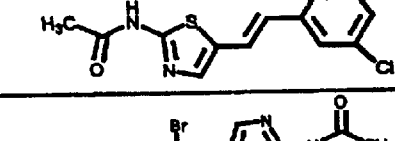
Figure 2:
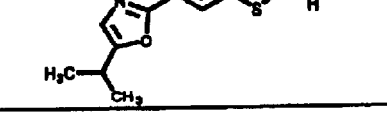
Figure 2:

We claim:
1. N-[(E)-5-(2-(5-t-Butyl-oxazol-2-yl)-vinyl)-thiazol-2-yl]-acetamide or a pharmaceutically acceptable salt thereof.
2. A pharmaceutical composition comprising the compound of claim 1 and a pharmaceutically acceptable carrier.

* * * * *